(12) United States Patent
Kopp

(10) Patent No.: US 12,137,995 B2
(45) Date of Patent: *Nov. 12, 2024

(54) ROBOTIC SURGICAL ASSEMBLIES AND INSTRUMENT DRIVE CONNECTORS THEREOF

(71) Applicant: Covidien LP, Mansfield, MA (US)

(72) Inventor: Brock Kopp, Colorado Springs, CO (US)

(73) Assignee: Covidien LP, Mansfield, MA (US)

( * ) Notice: Subject to any disclaimer, the term of this patent is extended or adjusted under 35 U.S.C. 154(b) by 23 days.

This patent is subject to a terminal disclaimer.

(21) Appl. No.: 18/083,760

(22) Filed: Dec. 19, 2022

(65) Prior Publication Data

US 2023/0125165 A1 Apr. 27, 2023

Related U.S. Application Data

(63) Continuation of application No. 17/024,925, filed on Sep. 18, 2020, now Pat. No. 11,529,203, which is a
(Continued)

(51) Int. Cl.
*A61B 34/30* (2016.01)
*A61B 17/00* (2006.01)
(Continued)

(52) U.S. Cl.
CPC ........ *A61B 34/30* (2016.02); *A61B 17/07207* (2013.01); *A61B 2017/00017* (2013.01);
(Continued)

(58) Field of Classification Search
USPC ...................................................... 227/175.2
See application file for complete search history.

(56) References Cited

U.S. PATENT DOCUMENTS 2,777,340 A 1/1957 Hettwer et al.
2,957,353 A 10/1960 Babacz
(Continued)

FOREIGN PATENT DOCUMENTS

CA 2451558 A1 1/2003
CN 1547454 A 11/2004
(Continued)

OTHER PUBLICATIONS

European Search Report and Written Opinion corresponding to counterpart Int'l Appln. No. PCT/US2016/052783 dated Jan. 4, 2017.
(Continued)

*Primary Examiner* — Joshua G Kotis
(74) *Attorney, Agent, or Firm* — Carter, DeLuca & Farrell LLP

(57) ABSTRACT

An instrument drive connector includes a housing assembly, an elongated shaft extending distally from the housing assembly, and a first drive assembly at least partially disposed within the housing assembly and the elongated shaft. The first drive assembly includes a first drive screw, a first input drive coupler non-rotatably coupled to a proximal end of the first drive screw, a first drive nut threadedly engaged with a threaded body portion of the first drive screw and longitudinally movable relative thereto in response to rotation of the first drive screw, and a locking link. The locking link includes an elongated body having a proximal end portion coupled to the first drive nut and longitudinally movable relative thereto between a proximal non-locking position and a distal locking position, and a distal end portion including a switch actuation assembly including a switch actuating arm biased towards the distal locking position.

19 Claims, 11 Drawing Sheets

Related U.S. Application Data continuation of application No. 15/758,986, filed as application No. PCT/US2016/052783 on Sep. 21, 2016, now Pat. No. 10,806,454.

(60) Provisional application No. 62/232,640, filed on Sep. 25, 2015.

(51) Int. Cl.
*A61B 17/072* (2006.01)
*A61B 90/00* (2016.01)
*A61B 90/98* (2016.01)

(52) U.S. Cl.
CPC ............ *A61B 2017/00137* (2013.01); *A61B 17/00234* (2013.01); *A61B 2017/00393* (2013.01); *A61B 2017/00398* (2013.01); *A61B 2017/0046* (2013.01); *A61B 2017/00473* (2013.01); *A61B 2017/00477* (2013.01); *A61B 2090/034* (2016.02); *A61B 2090/0808* (2016.02); *A61B 90/98* (2016.02)

(56) References Cited

U.S. PATENT DOCUMENTS

| | | |
|---|---|---|
| 3,111,328 A | 11/1963 | Di Rito et al. |
| 3,695,058 A | 10/1972 | Keith, Jr. |
| 3,734,515 A | 5/1973 | Dudek |
| 3,759,336 A | 9/1973 | Marcovitz et al. |
| 4,162,399 A | 7/1979 | Hudson |
| 4,606,343 A | 8/1986 | Conta et al. |
| 4,705,038 A | 11/1987 | Sjostrom et al. |
| 4,722,685 A | 2/1988 | de Estrada et al. |
| 4,823,807 A | 4/1989 | Russell et al. |
| 4,874,181 A | 10/1989 | Hsu |
| 5,129,118 A | 7/1992 | Walmesley |
| 5,129,570 A | 7/1992 | Schulze et al. |
| 5,152,744 A | 10/1992 | Krause et al. |
| 5,301,061 A | 4/1994 | Nakada et al. |
| 5,312,023 A | 5/1994 | Green et al. |
| 5,326,013 A | 7/1994 | Green et al. |
| 5,350,355 A | 9/1994 | Sklar |
| 5,383,874 A | 1/1995 | Jackson et al. |
| 5,383,880 A | 1/1995 | Hooven |
| 5,389,098 A | 2/1995 | Tsuruta et al. |
| 5,395,033 A | 3/1995 | Byrne et al. |
| 5,400,267 A | 3/1995 | Denen et al. |
| 5,411,508 A | 5/1995 | Bessler et al. |
| 5,413,267 A | 5/1995 | Solyntjes et al. |
| 5,427,087 A | 6/1995 | Ito et al. |
| 5,433,721 A | 7/1995 | Hooven et al. |
| 5,467,911 A | 11/1995 | Tsuruta et al. |
| 5,476,379 A | 12/1995 | Disel |
| 5,487,499 A | 1/1996 | Sorrentino et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,535,934 A | 7/1996 | Boiarski et al. |
| 5,535,937 A | 7/1996 | Boiarski et al. |
| 5,540,375 A | 7/1996 | Bolanos et al. |
| 5,540,706 A | 7/1996 | Aust et al. |
| 5,542,594 A | 8/1996 | McKean et al. |
| 5,549,637 A | 8/1996 | Crainich |
| 5,553,675 A | 9/1996 | Pitzen et al. |
| 5,562,239 A | 10/1996 | Boiarski et al. |
| 5,564,615 A | 10/1996 | Bishop et al. |
| 5,609,560 A | 3/1997 | Ichikawa et al. |
| 5,626,587 A | 5/1997 | Bishop et al. |
| 5,632,432 A | 5/1997 | Schulze et al. |
| 5,645,209 A | 7/1997 | Green et al. |
| 5,647,526 A | 7/1997 | Green et al. |
| 5,653,374 A | 8/1997 | Young et al. |
| 5,658,300 A | 8/1997 | Bito et al. |
| 5,662,662 A | 9/1997 | Bishop et al. |
| 5,667,517 A | 9/1997 | Hooven |
| 5,693,042 A | 12/1997 | Boiarski et al. |
| 5,704,534 A | 1/1998 | Huitema et al. |
| 5,713,505 A | 2/1998 | Huitema |
| 5,762,603 A | 6/1998 | Thompson |
| 5,779,130 A | 7/1998 | Alesi et al. |
| 5,782,396 A | 7/1998 | Mastri et al. |
| 5,782,397 A | 7/1998 | Koukline |
| 5,792,573 A | 8/1998 | Pitzen et al. |
| 5,797,536 A | 8/1998 | Smith et al. |
| 5,820,009 A | 10/1998 | Melling et al. |
| 5,863,159 A | 1/1999 | Lasko |
| 5,865,361 A | 2/1999 | Milliman et al. |
| 5,908,427 A | 6/1999 | McKean et al. |
| 5,954,259 A | 9/1999 | Viola et al. |
| 5,964,774 A | 10/1999 | McKean et al. |
| 5,993,454 A | 11/1999 | Longo |
| 6,010,054 A | 1/2000 | Johnson et al. |
| 6,017,354 A | 1/2000 | Culp et al. |
| 6,032,849 A | 3/2000 | Mastri et al. |
| 6,045,560 A | 4/2000 | McKean et al. |
| 6,090,123 A | 7/2000 | Culp et al. |
| 6,126,651 A | 10/2000 | Mayer |
| 6,129,547 A | 10/2000 | Cise et al. |
| 6,132,368 A | 10/2000 | Cooper |
| 6,165,169 A | 12/2000 | Panescu et al. |
| 6,206,903 B1 | 3/2001 | Ramans |
| 6,239,732 B1 | 5/2001 | Cusey |
| 6,241,139 B1 | 6/2001 | Milliman et al. |
| 6,246,200 B1 | 6/2001 | Blumenkranz et al. |
| 6,264,086 B1 | 7/2001 | McGuckin, Jr. |
| 6,264,087 B1 | 7/2001 | Whitman |
| 6,302,311 B1 | 10/2001 | Adams et al. |
| 6,312,435 B1 | 11/2001 | Wallace et al. |
| 6,315,184 B1 | 11/2001 | Whitman |
| 6,321,855 B1 | 11/2001 | Barnes |
| 6,329,778 B1 | 12/2001 | Culp et al. |
| 6,331,181 B1 | 12/2001 | Tierney et al. |
| 6,343,731 B1 | 2/2002 | Adams et al. |
| 6,348,061 B1 | 2/2002 | Whitman |
| 6,368,324 B1 | 4/2002 | Dinger et al. |
| 6,371,909 B1 | 4/2002 | Hoeg et al. |
| 6,394,998 B1 | 5/2002 | Wallace et al. |
| 6,424,885 B1 | 7/2002 | Niemeyer et al. |
| 6,434,507 B1 | 8/2002 | Clayton et al. |
| 6,441,577 B2 | 8/2002 | Blumenkranz et al. |
| 6,443,973 B1 | 9/2002 | Whitman |
| 6,459,926 B1 | 10/2002 | Nowlin et al. |
| 6,461,372 B1 | 10/2002 | Jensen et al. |
| 6,488,197 B1 | 12/2002 | Whitman |
| 6,491,201 B1 | 12/2002 | Whitman |
| 6,491,691 B1 | 12/2002 | Morley et al. |
| 6,491,701 B2 | 12/2002 | Tierney et al. |
| 6,493,608 B1 | 12/2002 | Niemeyer |
| 6,533,157 B1 | 3/2003 | Whitman |
| 6,537,280 B2 | 3/2003 | Dinger et al. |
| 6,565,554 B1 | 5/2003 | Niemeyer |
| 6,610,066 B2 | 8/2003 | Dinger et al. |
| 6,611,793 B1 | 8/2003 | Burnside et al. |
| 6,645,196 B1 | 11/2003 | Nixon et al. |
| 6,645,218 B1 | 11/2003 | Cassidy et al. |
| 6,654,999 B2 | 12/2003 | Stoddard et al. |
| 6,659,939 B2 | 12/2003 | Moll |
| 6,671,581 B2 | 12/2003 | Niemeyer et al. |
| 6,676,684 B1 | 1/2004 | Morley et al. |
| 6,685,698 B2 | 2/2004 | Morley et al. |
| 6,698,643 B2 | 3/2004 | Whitman |
| 6,699,177 B1 | 3/2004 | Wang et al. |
| 6,699,235 B2 | 3/2004 | Wallace et al. |
| 6,714,839 B2 | 3/2004 | Salisbury, Jr. et al. |
| 6,716,233 B1 | 4/2004 | Whitman |
| 6,728,599 B2 | 4/2004 | Wang et al. |
| 6,743,240 B2 | 6/2004 | Smith et al. |
| 6,746,443 B1 | 6/2004 | Morley et al. |
| 6,766,204 B2 | 7/2004 | Niemeyer et al. |
| 6,770,081 B1 | 8/2004 | Cooper et al. |
| 6,772,053 B2 | 8/2004 | Niemeyer |
| 6,783,524 B2 | 8/2004 | Anderson et al. |
| 6,783,533 B2 | 8/2004 | Green et al. |

(56) References Cited

U.S. PATENT DOCUMENTS

| | | |
|---|---|---|
| 6,792,390 B1 | 9/2004 | Burnside et al. |
| 6,793,652 B1 | 9/2004 | Whitman et al. |
| 6,793,653 B2 | 9/2004 | Sanchez et al. |
| 6,799,065 B1 | 9/2004 | Niemeyer |
| 6,817,508 B1 | 11/2004 | Racenet et al. |
| 6,830,174 B2 | 12/2004 | Hillstead et al. |
| 6,837,883 B2 | 1/2005 | Moll et al. |
| 6,839,612 B2 | 1/2005 | Sanchez et al. |
| 6,840,938 B1 | 1/2005 | Morley et al. |
| 6,843,403 B2 | 1/2005 | Whitman |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,860,892 B1 | 3/2005 | Tanaka et al. |
| 6,866,671 B2 | 3/2005 | Tierney et al. |
| 6,871,117 B2 | 3/2005 | Wang et al. |
| 6,879,880 B2 | 4/2005 | Nowlin et al. |
| 6,899,538 B2 | 5/2005 | Matoba |
| 6,899,705 B2 | 5/2005 | Niemeyer |
| 6,902,560 B1 | 6/2005 | Morley et al. |
| 6,905,057 B2 | 6/2005 | Swayze et al. |
| 6,936,042 B2 | 8/2005 | Wallace et al. |
| 6,951,535 B2 | 10/2005 | Ghodoussi et al. |
| 6,959,852 B2 | 11/2005 | Shelton, IV et al. |
| 6,964,363 B2 | 11/2005 | Wales et al. |
| 6,974,449 B2 | 12/2005 | Niemeyer |
| 6,981,628 B2 | 1/2006 | Wales |
| 6,981,941 B2 | 1/2006 | Whitman et al. |
| 6,986,451 B1 | 1/2006 | Mastri et al. |
| 6,988,649 B2 | 1/2006 | Shelton, IV et al. |
| 6,991,627 B2 | 1/2006 | Madhani et al. |
| 6,994,708 B2 | 2/2006 | Manzo |
| 7,032,798 B2 | 4/2006 | Whitman et al. |
| 7,048,745 B2 | 5/2006 | Tierney et al. |
| RE39,152 E | 6/2006 | Aust et al. |
| 7,055,731 B2 | 6/2006 | Shelton, IV et al. |
| 7,059,508 B2 | 6/2006 | Shelton, IV et al. |
| 7,066,926 B2 | 6/2006 | Wallace et al. |
| 7,077,856 B2 | 7/2006 | Whitman |
| 7,111,769 B2 | 9/2006 | Wales et al. |
| 7,118,582 B1 | 10/2006 | Wang et al. |
| 7,122,029 B2 | 10/2006 | Koop et al. |
| 7,125,403 B2 | 10/2006 | Julian et al. |
| 7,140,528 B2 | 11/2006 | Shelton, IV |
| 7,141,049 B2 | 11/2006 | Stern et al. |
| 7,143,923 B2 | 12/2006 | Shelton, IV et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,155,315 B2 | 12/2006 | Niemeyer et al. |
| 7,172,104 B2 | 2/2007 | Scirica et al. |
| 7,225,964 B2 | 6/2007 | Mastri et al. |
| 7,238,021 B1 | 7/2007 | Johnson |
| 7,239,940 B2 | 7/2007 | Wang et al. |
| 7,246,734 B2 | 7/2007 | Shelton, IV |
| 7,252,660 B2 | 8/2007 | Kunz |
| 7,306,597 B2 | 12/2007 | Manzo |
| 7,328,828 B2 | 2/2008 | Ortiz et al. |
| 7,357,774 B2 | 4/2008 | Cooper |
| 7,364,061 B2 | 4/2008 | Swayze et al. |
| 7,373,219 B2 | 5/2008 | Nowlin et al. |
| 7,379,790 B2 | 5/2008 | Toth et al. |
| 7,380,695 B2 | 6/2008 | Doll et al. |
| 7,380,696 B2 | 6/2008 | Shelton, IV et al. |
| 7,386,365 B2 | 6/2008 | Nixon |
| 7,391,173 B2 | 6/2008 | Schena |
| 7,398,707 B2 | 7/2008 | Morley et al. |
| 7,404,508 B2 | 7/2008 | Smith et al. |
| 7,407,078 B2 | 8/2008 | Shelton, IV et al. |
| 7,413,565 B2 | 8/2008 | Wang et al. |
| 7,416,101 B2 | 8/2008 | Shelton, IV et al. |
| 7,419,080 B2 | 9/2008 | Smith et al. |
| 7,422,139 B2 | 9/2008 | Shelton, IV et al. |
| 7,431,189 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,453,227 B2 | 11/2008 | Prisco et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,347 B2 | 1/2009 | Roy |
| 7,481,824 B2 | 1/2009 | Boudreaux et al. |
| 7,487,899 B2 | 2/2009 | Shelton, IV et al. |
| 7,524,320 B2 | 4/2009 | Tierney et al. |
| 7,549,564 B2 | 6/2009 | Boudreaux |
| 7,565,993 B2 | 7/2009 | Milliman et al. |
| 7,568,603 B2 | 8/2009 | Shelton, IV et al. |
| 7,574,250 B2 | 8/2009 | Niemeyer |
| 7,575,144 B2 | 8/2009 | Ortiz et al. |
| 7,588,175 B2 | 9/2009 | Timm et al. |
| 7,588,176 B2 | 9/2009 | Timm et al. |
| 7,594,912 B2 | 9/2009 | Cooper et al. |
| 7,607,440 B2 | 10/2009 | Coste-Maniere et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,666,191 B2 | 2/2010 | Orban, III et al. |
| 7,670,334 B2 | 3/2010 | Hueil et al. |
| 7,673,780 B2 | 3/2010 | Shelton, IV et al. |
| 7,682,357 B2 | 3/2010 | Ghodoussi et al. |
| 7,689,320 B2 | 3/2010 | Prisco et al. |
| 7,695,481 B2 | 4/2010 | Wang et al. |
| 7,695,485 B2 | 4/2010 | Whitman et al. |
| 7,699,835 B2 | 4/2010 | Lee et al. |
| 7,699,855 B2 | 4/2010 | Anderson et al. |
| 7,713,263 B2 | 5/2010 | Niemeyer |
| 7,721,931 B2 | 5/2010 | Shelton, IV et al. |
| 7,725,214 B2 | 5/2010 | Diolaiti |
| 7,727,244 B2 | 6/2010 | Orban, III et al. |
| 7,738,971 B2 | 6/2010 | Swayze et al. |
| 7,740,159 B2 | 6/2010 | Shelton, IV et al. |
| 7,741,802 B2 | 6/2010 | Prisco |
| 7,743,960 B2 | 6/2010 | Whitman et al. |
| 7,756,036 B2 | 7/2010 | Druke et al. |
| 7,757,028 B2 | 7/2010 | Druke et al. |
| 7,758,613 B2 | 7/2010 | Whitman |
| 7,762,825 B2 | 7/2010 | Burbank et al. |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,778,733 B2 | 8/2010 | Nowlin et al. |
| 7,793,812 B2 | 9/2010 | Moore et al. |
| 7,799,039 B2 | 9/2010 | Shelton, IV et al. |
| 7,802,712 B2 | 9/2010 | Milliman et al. |
| 7,803,151 B2 | 9/2010 | Whitman |
| 7,806,891 B2 | 10/2010 | Nowlin et al. |
| 7,819,859 B2 | 10/2010 | Prisco et al. |
| 7,819,885 B2 | 10/2010 | Cooper |
| 7,822,458 B2 | 10/2010 | Webster, III et al. |
| 7,824,401 B2 | 11/2010 | Manzo et al. |
| 7,835,823 B2 | 11/2010 | Sillman et al. |
| 7,843,158 B2 | 11/2010 | Prisco |
| 7,845,534 B2 | 12/2010 | Viola et al. |
| 7,845,537 B2 | 12/2010 | Shelton, IV et al. |
| 7,857,185 B2 | 12/2010 | Swayze et al. |
| 7,865,266 B2 | 1/2011 | Moll et al. |
| 7,865,269 B2 | 1/2011 | Prisco et al. |
| 7,870,989 B2 | 1/2011 | Viola et al. |
| 7,886,743 B2 | 2/2011 | Cooper et al. |
| 7,899,578 B2 | 3/2011 | Prisco et al. |
| 7,900,805 B2 | 3/2011 | Shelton, IV et al. |
| 7,905,897 B2 | 3/2011 | Whitman et al. |
| 7,907,166 B2 | 3/2011 | Lamprecht et al. |
| 7,918,230 B2 | 4/2011 | Whitman et al. |
| 7,922,061 B2 | 4/2011 | Shelton, IV et al. |
| 7,922,719 B2 | 4/2011 | Ralph et al. |
| 7,935,130 B2 | 5/2011 | Williams |
| 7,947,034 B2 | 5/2011 | Whitman |
| 7,951,071 B2 | 5/2011 | Whitman et al. |
| 7,954,682 B2 | 6/2011 | Giordano et al. |
| 7,959,051 B2 | 6/2011 | Smith et al. |
| 7,963,433 B2 | 6/2011 | Whitman et al. |
| 7,963,913 B2 | 6/2011 | Devengenzo et al. |
| 7,967,178 B2 | 6/2011 | Scirica et al. |

(56) References Cited

U.S. PATENT DOCUMENTS

| | | |
|---|---|---|
| 7,967,179 B2 | 6/2011 | Olson et al. |
| 7,983,793 B2 | 7/2011 | Toth et al. |
| 7,992,758 B2 | 8/2011 | Whitman et al. |
| 8,002,767 B2 | 8/2011 | Sanchez |
| 8,004,229 B2 | 8/2011 | Nowlin et al. |
| 8,011,550 B2 | 9/2011 | Aranyi et al. |
| 8,012,170 B2 | 9/2011 | Whitman et al. |
| 8,016,178 B2 | 9/2011 | Olson et al. |
| 8,016,855 B2 | 9/2011 | Whitman et al. |
| 8,020,743 B2 | 9/2011 | Shelton, IV |
| 8,025,199 B2 | 9/2011 | Whitman et al. |
| 8,035,487 B2 | 10/2011 | Malackowski |
| 8,052,024 B2 | 11/2011 | Viola et al. |
| 8,054,752 B2 | 11/2011 | Druke et al. |
| 8,056,787 B2 | 11/2011 | Boudreaux et al. |
| 8,062,288 B2 | 11/2011 | Cooper et al. |
| 8,079,950 B2 | 12/2011 | Stern et al. |
| 8,100,133 B2 | 1/2012 | Mintz et al. |
| 8,108,072 B2 | 1/2012 | Zhao et al. |
| 8,114,118 B2 | 2/2012 | Knodel et al. |
| 8,120,301 B2 | 2/2012 | Goldberg et al. |
| 8,127,975 B2 | 3/2012 | Olson et al. |
| 8,132,705 B2 | 3/2012 | Viola et al. |
| 8,142,447 B2 | 3/2012 | Cooper et al. |
| 8,147,503 B2 | 4/2012 | Zhao et al. |
| 8,151,661 B2 | 4/2012 | Schena et al. |
| 8,152,516 B2 | 4/2012 | Harvey et al. |
| 8,155,479 B2 | 4/2012 | Hoffman et al. |
| 8,157,150 B2 | 4/2012 | Viola et al. |
| 8,157,151 B2 | 4/2012 | Ingmanson et al. |
| 8,182,469 B2 | 5/2012 | Anderson et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,202,278 B2 | 6/2012 | Orban, III et al. |
| 8,206,406 B2 | 6/2012 | Orban, III |
| 8,210,413 B2 | 7/2012 | Whitman et al. |
| 8,216,250 B2 | 7/2012 | Orban, III et al. |
| 8,220,367 B2 | 7/2012 | Hsu |
| 8,220,468 B2 | 7/2012 | Cooper et al. |
| 8,235,273 B2 | 8/2012 | Olson et al. |
| 8,241,322 B2 | 8/2012 | Whitman et al. |
| 8,256,319 B2 | 9/2012 | Cooper et al. |
| 8,272,554 B2 | 9/2012 | Whitman et al. |
| 8,285,517 B2 | 10/2012 | Sillman et al. |
| 8,292,150 B2 | 10/2012 | Bryant |
| 8,292,888 B2 | 10/2012 | Whitman |
| 8,303,581 B2 | 11/2012 | Arts et al. |
| 8,315,720 B2 | 11/2012 | Mohr et al. |
| 8,335,590 B2 | 12/2012 | Costa et al. |
| 8,342,379 B2 | 1/2013 | Whitman et al. |
| 8,347,757 B2 | 1/2013 | Duval |
| 8,348,130 B2 | 1/2013 | Shah et al. |
| 8,348,855 B2 | 1/2013 | Hillely et al. |
| 8,353,440 B2 | 1/2013 | Whitman et al. |
| 8,357,144 B2 | 1/2013 | Whitman et al. |
| 8,365,633 B2 | 2/2013 | Simaan et al. |
| 8,365,972 B2 | 2/2013 | Aranyi et al. |
| 8,371,492 B2 | 2/2013 | Aranyi et al. |
| 8,372,057 B2 | 2/2013 | Cude et al. |
| 8,374,723 B2 | 2/2013 | Zhao et al. |
| 8,391,957 B2 | 3/2013 | Carlson et al. |
| 8,403,926 B2 | 3/2013 | Nobis et al. |
| 8,403,949 B2 | 3/2013 | Palmer et al. |
| 8,418,073 B2 | 4/2013 | Mohr et al. |
| 8,418,904 B2 | 4/2013 | Wenchell et al. |
| 8,419,717 B2 | 4/2013 | Diolaiti et al. |
| 8,423,182 B2 | 4/2013 | Robinson et al. |
| 8,424,739 B2 | 4/2013 | Racenet et al. |
| 8,452,447 B2 | 5/2013 | Nixon |
| 8,454,585 B2 | 6/2013 | Whitman |
| 8,499,992 B2 | 8/2013 | Whitman et al. |
| 8,505,802 B2 | 8/2013 | Viola et al. |
| 8,508,173 B2 | 8/2013 | Goldberg et al. |
| 8,517,241 B2 | 8/2013 | Nicholas et al. |
| 8,523,043 B2 | 9/2013 | Ullrich et al. |
| 8,528,440 B2 | 9/2013 | Morley et al. |
| 8,529,582 B2 | 9/2013 | Devengenzo et al. |
| 8,540,748 B2 | 9/2013 | Murphy et al. |
| 8,551,076 B2 | 10/2013 | Duval et al. |
| 8,551,116 B2 | 10/2013 | Julian et al. |
| 8,561,871 B2 | 10/2013 | Rajappa et al. |
| 8,561,874 B2 | 10/2013 | Scirica |
| 8,562,594 B2 | 10/2013 | Cooper et al. |
| 8,594,841 B2 | 11/2013 | Zhao et al. |
| 8,597,182 B2 | 12/2013 | Stein et al. |
| 8,597,280 B2 | 12/2013 | Cooper et al. |
| 8,600,551 B2 | 12/2013 | Itkowitz et al. |
| 8,602,287 B2 | 12/2013 | Yates et al. |
| 8,608,773 B2 | 12/2013 | Tierney et al. |
| 8,620,473 B2 | 12/2013 | Diolaiti et al. |
| 8,623,000 B2 | 1/2014 | Humayun et al. |
| 8,624,537 B2 | 1/2014 | Nowlin et al. |
| 8,627,995 B2 | 1/2014 | Smith et al. |
| 8,632,463 B2 | 1/2014 | Drinan et al. |
| 8,634,957 B2 | 1/2014 | Toth et al. |
| 8,636,766 B2 | 1/2014 | Milliman et al. |
| 8,638,056 B2 | 1/2014 | Goldberg et al. |
| 8,638,057 B2 | 1/2014 | Goldberg et al. |
| 8,644,988 B2 | 2/2014 | Prisco et al. |
| 8,647,258 B2 | 2/2014 | Aranyi et al. |
| 8,652,121 B2 | 2/2014 | Quick et al. |
| 8,657,174 B2 | 2/2014 | Yates et al. |
| 8,657,177 B2 | 2/2014 | Scirica et al. |
| 8,666,544 B2 | 3/2014 | Moll et al. |
| 8,668,638 B2 | 3/2014 | Donhowe et al. |
| 8,672,206 B2 | 3/2014 | Aranyi et al. |
| 8,696,552 B2 | 4/2014 | Whitman |
| 8,708,213 B2 | 4/2014 | Shelton, IV et al. |
| 8,715,306 B2 | 5/2014 | Faller et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,752,749 B2 | 6/2014 | Moore et al. |
| 8,758,352 B2 | 6/2014 | Cooper et al. |
| 8,758,391 B2 | 6/2014 | Swayze et al. |
| 8,761,930 B2 | 6/2014 | Nixon |
| 8,768,516 B2 | 7/2014 | Diolaiti et al. |
| 8,786,241 B2 | 7/2014 | Nowlin et al. |
| 8,790,243 B2 | 7/2014 | Cooper et al. |
| 8,806,973 B2 | 8/2014 | Ross et al. |
| 8,808,164 B2 | 8/2014 | Hoffman et al. |
| 8,808,311 B2 | 8/2014 | Heinrich et al. |
| 8,816,628 B2 | 8/2014 | Nowlin et al. |
| 8,820,605 B2 | 9/2014 | Shelton, IV |
| 8,821,480 B2 | 9/2014 | Burbank |
| 8,823,308 B2 | 9/2014 | Nowlin et al. |
| 8,827,989 B2 | 9/2014 | Niemeyer |
| 8,838,270 B2 | 9/2014 | Druke et al. |
| 8,851,355 B2 | 10/2014 | Aranyi et al. |
| 8,852,174 B2 | 10/2014 | Burbank |
| 8,858,547 B2 | 10/2014 | Brogna |
| 8,858,571 B2 | 10/2014 | Shelton, IV et al. |
| 8,862,268 B2 | 10/2014 | Robinson et al. |
| 8,864,751 B2 | 10/2014 | Prisco et al. |
| 8,864,752 B2 | 10/2014 | Diolaiti et al. |
| 8,875,972 B2 | 11/2014 | Weisenburgh, II et al. |
| 8,888,762 B2 | 11/2014 | Whitman |
| 8,893,946 B2 | 11/2014 | Boudreaux et al. |
| 8,899,462 B2 | 12/2014 | Kostrzewski et al. |
| 8,903,546 B2 | 12/2014 | Diolaiti et al. |
| 8,903,549 B2 | 12/2014 | Itkowitz et al. |
| 8,905,289 B2 | 12/2014 | Patel et al. |
| 8,911,428 B2 | 12/2014 | Cooper et al. |
| 8,912,746 B2 | 12/2014 | Reid et al. |
| 8,919,630 B2 | 12/2014 | Milliman |
| 8,931,680 B2 | 1/2015 | Milliman |
| 8,939,344 B2 | 1/2015 | Olson et al. |
| 8,944,070 B2 | 2/2015 | Guthart |
| 8,950,646 B2 | 2/2015 | Viola |
| 8,960,519 B2 | 2/2015 | Whitman et al. |
| 8,961,396 B2 | 2/2015 | Azarbarzin et al. |
| 8,967,443 B2 | 3/2015 | McCuen |
| 8,968,276 B2 | 3/2015 | Zemlok et al. |

(56) References Cited

U.S. PATENT DOCUMENTS

| | | |
|---|---|---|
| 8,968,337 B2 | 3/2015 | Whitfield et al. |
| 8,989,903 B2 | 3/2015 | Weir et al. |
| 8,992,422 B2 | 3/2015 | Spivey et al. |
| 9,002,518 B2 | 4/2015 | Manzo |
| 9,014,856 B2 | 4/2015 | Manzo et al. |
| 9,016,540 B2 | 4/2015 | Whitman et al. |
| 9,016,545 B2 | 4/2015 | Aranyi et al. |
| 9,019,345 B2 | 4/2015 | O'Grady et al. |
| 9,023,014 B2 | 5/2015 | Chowaniec et al. |
| 9,033,868 B2 | 5/2015 | Whitman et al. |
| 9,043,027 B2 | 5/2015 | Durant et al. |
| 9,050,120 B2 | 6/2015 | Swarup et al. |
| 9,055,943 B2 | 6/2015 | Zemlok et al. |
| 9,055,961 B2 | 6/2015 | Manzo et al. |
| 9,064,653 B2 | 6/2015 | Prest et al. |
| 9,068,628 B2 | 6/2015 | Solomon et al. |
| 9,072,515 B2 | 7/2015 | Hall et al. |
| 9,078,684 B2 | 7/2015 | Williams |
| 9,084,623 B2 | 7/2015 | Gomez et al. |
| 9,095,362 B2 | 8/2015 | Dachs, II et al. |
| 9,096,033 B2 | 8/2015 | Holop et al. |
| 9,101,381 B2 | 8/2015 | Burbank et al. |
| 9,113,847 B2 | 8/2015 | Whitman et al. |
| 9,113,875 B2 | 8/2015 | Viola et al. |
| 9,113,876 B2 | 8/2015 | Zemlok et al. |
| 9,113,877 B1 | 8/2015 | Whitman et al. |
| 9,113,899 B2 | 8/2015 | Garrison et al. |
| 9,138,284 B2 | 9/2015 | Krom et al. |
| 9,144,456 B2 | 9/2015 | Rosa et al. |
| 9,198,730 B2 | 12/2015 | Prisco et al. |
| 9,204,923 B2 | 12/2015 | Manzo et al. |
| 9,216,013 B2 | 12/2015 | Scirica et al. |
| 9,226,648 B2 | 1/2016 | Saadat et al. |
| 9,226,750 B2 | 1/2016 | Weir et al. |
| 9,226,761 B2 | 1/2016 | Burbank |
| 9,232,984 B2 | 1/2016 | Guthart et al. |
| 9,241,712 B2 | 1/2016 | Zemlok et al. |
| 9,241,766 B2 | 1/2016 | Duque et al. |
| 9,241,767 B2 | 1/2016 | Prisco et al. |
| 9,241,769 B2 | 1/2016 | Larkin et al. |
| 9,259,275 B2 | 2/2016 | Burbank |
| 9,259,277 B2 | 2/2016 | Rogers et al. |
| 9,259,281 B2 | 2/2016 | Griffiths et al. |
| 9,259,282 B2 | 2/2016 | Azizian et al. |
| 9,261,172 B2 | 2/2016 | Solomon et al. |
| 9,265,567 B2 | 2/2016 | Orban, III et al. |
| 9,265,584 B2 | 2/2016 | Itkowitz et al. |
| 9,282,961 B2 | 3/2016 | Whitman et al. |
| 9,282,963 B2 | 3/2016 | Bryant |
| 9,283,049 B2 | 3/2016 | Diolaiti et al. |
| 9,295,522 B2 | 3/2016 | Kostrzewski |
| 9,301,811 B2 | 4/2016 | Goldberg et al. |
| 9,307,986 B2 | 4/2016 | Hall et al. |
| 9,314,307 B2 | 4/2016 | Richmond et al. |
| 9,317,651 B2 | 4/2016 | Nixon |
| 9,345,546 B2 | 5/2016 | Toth et al. |
| 9,393,017 B2 | 7/2016 | Flanagan et al. |
| 9,402,689 B2 | 8/2016 | Prisco et al. |
| 9,417,621 B2 | 8/2016 | Diolaiti |
| 9,424,303 B2 | 8/2016 | Hoffman et al. |
| 9,433,418 B2 | 9/2016 | Whitman et al. |
| 9,446,517 B2 | 9/2016 | Burns et al. |
| 9,452,020 B2 | 9/2016 | Griffiths et al. |
| 9,474,569 B2 | 10/2016 | Manzo et al. |
| 9,480,533 B2 | 11/2016 | Devengenzo et al. |
| 9,503,713 B2 | 11/2016 | Zhao et al. |
| 9,550,300 B2 | 1/2017 | Danitz et al. |
| 9,554,859 B2 | 1/2017 | Nowlin et al. |
| 9,566,124 B2 | 2/2017 | Prisco et al. |
| 9,579,164 B2 | 2/2017 | Itkowitz et al. |
| 9,585,641 B2 | 3/2017 | Cooper et al. |
| 9,615,883 B2 | 4/2017 | Schena et al. |
| 9,623,563 B2 | 4/2017 | Nixon |
| 9,623,902 B2 | 4/2017 | Griffiths et al. |
| 9,629,520 B2 | 4/2017 | Diolaiti |
| 9,662,177 B2 | 5/2017 | Weir et al. |
| 9,664,262 B2 | 5/2017 | Donlon et al. |
| 9,687,312 B2 | 6/2017 | Dachs, II et al. |
| 9,700,334 B2 | 7/2017 | Hinman et al. |
| 9,718,190 B2 | 8/2017 | Larkin et al. |
| 9,730,719 B2 | 8/2017 | Brisson et al. |
| 9,737,199 B2 | 8/2017 | Pistor et al. |
| 9,795,446 B2 | 10/2017 | DiMaio et al. |
| 9,797,484 B2 | 10/2017 | Solomon et al. |
| 9,801,646 B2 | 10/2017 | Zergiebel |
| 9,801,690 B2 | 10/2017 | Larkin et al. |
| 9,814,530 B2 | 11/2017 | Weir et al. |
| 9,814,536 B2 | 11/2017 | Goldberg et al. |
| 9,814,537 B2 | 11/2017 | Itkowitz et al. |
| 9,820,823 B2 | 11/2017 | Richmond et al. |
| 9,827,059 B2 | 11/2017 | Robinson et al. |
| 9,830,371 B2 | 11/2017 | Hoffman et al. |
| 9,839,481 B2 | 12/2017 | Blumenkranz et al. |
| 9,839,487 B2 | 12/2017 | Dachs, II |
| 9,850,994 B2 | 12/2017 | Schena |
| 9,855,102 B2 | 1/2018 | Blumenkranz |
| 9,855,107 B2 | 1/2018 | Labonville et al. |
| 9,872,737 B2 | 1/2018 | Nixon |
| 9,877,718 B2 | 1/2018 | Weir et al. |
| 9,883,920 B2 | 2/2018 | Blumenkranz |
| 9,888,974 B2 | 2/2018 | Niemeyer |
| 9,895,813 B2 | 2/2018 | Blumenkranz et al. |
| 9,901,408 B2 | 2/2018 | Larkin |
| 9,918,800 B2 | 3/2018 | Itkowitz et al. |
| 9,943,375 B2 | 4/2018 | Blumenkranz et al. |
| 9,948,852 B2 | 4/2018 | Lilagan et al. |
| 9,949,798 B2 | 4/2018 | Weir |
| 9,949,802 B2 | 4/2018 | Cooper |
| 9,952,107 B2 | 4/2018 | Blumenkranz et al. |
| 9,956,044 B2 | 5/2018 | Gomez et al. |
| 9,980,778 B2 | 5/2018 | Ohline et al. |
| 10,008,017 B2 | 6/2018 | Itkowitz et al. |
| 10,028,793 B2 | 7/2018 | Griffiths et al. |
| 10,033,308 B2 | 7/2018 | Chaghajerdi et al. |
| 10,034,719 B2 | 7/2018 | Richmond et al. |
| 10,052,167 B2 | 8/2018 | Au et al. |
| 10,085,811 B2 | 10/2018 | Weir et al. |
| 10,092,344 B2 | 10/2018 | Mohr et al. |
| 10,123,844 B2 | 11/2018 | Nowlin |
| 10,188,471 B2 | 1/2019 | Brisson |
| 10,201,390 B2 | 2/2019 | Swarup et al. |
| 10,213,202 B2 | 2/2019 | Flanagan et al. |
| 10,238,391 B2 | 3/2019 | Leimbach et al. |
| 10,258,333 B2 | 4/2019 | Shelton, IV et al. |
| 10,258,416 B2 | 4/2019 | Mintz et al. |
| 10,278,782 B2 | 5/2019 | Jarc et al. |
| 10,278,783 B2 | 5/2019 | Itkowitz et al. |
| 10,282,881 B2 | 5/2019 | Itkowitz et al. |
| 10,335,242 B2 | 7/2019 | Devengenzo et al. |
| 10,405,934 B2 | 9/2019 | Prisco et al. |
| 10,433,922 B2 | 10/2019 | Itkowitz et al. |
| 10,464,219 B2 | 11/2019 | Robinson et al. |
| 10,485,621 B2 | 11/2019 | Morrissette et al. |
| 10,500,004 B2 | 12/2019 | Hanuschik et al. |
| 10,500,005 B2 | 12/2019 | Weir et al. |
| 10,500,007 B2 | 12/2019 | Richmond et al. |
| 10,507,066 B2 | 12/2019 | DiMaio et al. |
| 10,510,267 B2 | 12/2019 | Jarc et al. |
| 10,524,871 B2 | 1/2020 | Liao |
| 10,548,459 B2 | 2/2020 | Itkowitz et al. |
| 10,575,909 B2 | 3/2020 | Robinson et al. |
| 10,592,529 B2 | 3/2020 | Hoffman et al. |
| 10,595,946 B2 | 3/2020 | Nixon |
| 10,806,454 B2 * | 10/2020 | Kopp ................ A61B 34/30 |
| 10,881,469 B2 | 1/2021 | Robinson |
| 10,881,473 B2 | 1/2021 | Itkowitz et al. |
| 10,898,188 B2 | 1/2021 | Burbank |
| 10,898,189 B2 | 1/2021 | McDonald, II |
| 10,905,506 B2 | 2/2021 | Itkowitz et al. |
| 10,912,544 B2 | 2/2021 | Brisson et al. |
| 10,912,619 B2 | 2/2021 | Jarc et al. |
| 10,918,387 B2 | 2/2021 | Duque et al. |
| 10,918,449 B2 | 2/2021 | Solomon et al. |
| 10,932,873 B2 | 3/2021 | Griffiths et al. |

(56) References Cited

U.S. PATENT DOCUMENTS

| | | |
|---|---|---|
| 10,932,877 B2 | 3/2021 | Devengenzo et al. |
| 10,939,969 B2 | 3/2021 | Swarup et al. |
| 10,939,973 B2 | 3/2021 | DiMaio et al. |
| 10,952,801 B2 | 3/2021 | Miller et al. |
| 10,965,933 B2 | 3/2021 | Jarc |
| 10,966,742 B2 | 4/2021 | Rosa et al. |
| 10,973,517 B2 | 4/2021 | Wixey |
| 10,973,519 B2 | 4/2021 | Weir et al. |
| 10,984,567 B2 | 4/2021 | Itkowitz et al. |
| 10,993,773 B2 | 5/2021 | Cooper et al. |
| 10,993,775 B2 | 5/2021 | Cooper et al. |
| 11,000,331 B2 | 5/2021 | Krom et al. |
| 11,013,567 B2 | 5/2021 | Wu et al. |
| 11,020,138 B2 | 6/2021 | Ragosta |
| 11,020,191 B2 | 6/2021 | Diolaiti et al. |
| 11,020,193 B2 | 6/2021 | Wixey et al. |
| 11,026,755 B2 | 6/2021 | Weir et al. |
| 11,026,759 B2 | 6/2021 | Donlon et al. |
| 11,040,189 B2 | 6/2021 | Vaders et al. |
| 11,045,077 B2 | 6/2021 | Stern et al. |
| 11,045,274 B2 | 6/2021 | Dachs, II et al. |
| 11,058,501 B2 | 7/2021 | Tokarchuk et al. |
| 11,076,925 B2 | 8/2021 | DiMaio et al. |
| 11,090,119 B2 | 8/2021 | Burbank |
| 11,096,687 B2 | 8/2021 | Flanagan et al. |
| 11,098,803 B2 | 8/2021 | Duque et al. |
| 11,109,925 B2 | 9/2021 | Cooper et al. |
| 11,116,578 B2 | 9/2021 | Hoffman et al. |
| 11,129,683 B2 | 9/2021 | Steger et al. |
| 11,135,029 B2 | 10/2021 | Suresh et al. |
| 11,147,552 B2 | 10/2021 | Burbank et al. |
| 11,147,640 B2 | 10/2021 | Jarc et al. |
| 11,154,373 B2 | 10/2021 | Abbott et al. |
| 11,154,374 B2 | 10/2021 | Hanuschik et al. |
| 11,160,622 B2 | 11/2021 | Goldberg et al. |
| 11,160,625 B2 | 11/2021 | Wixey et al. |
| 11,161,243 B2 | 11/2021 | Rabindran et al. |
| 11,166,758 B2 | 11/2021 | Mohr et al. |
| 11,166,770 B2 | 11/2021 | DiMaio et al. |
| 11,166,773 B2 | 11/2021 | Ragosta et al. |
| 11,173,597 B2 | 11/2021 | Rabindran et al. |
| 11,185,378 B2 | 11/2021 | Weir et al. |
| 11,191,596 B2 | 12/2021 | Thompson et al. |
| 11,197,729 B2 | 12/2021 | Thompson et al. |
| 11,213,360 B2 | 1/2022 | Hourtash et al. |
| 11,221,863 B2 | 1/2022 | Azizian et al. |
| 11,234,700 B2 | 2/2022 | Ragosta et al. |
| 11,241,274 B2 | 2/2022 | Vaders et al. |
| 11,241,290 B2 | 2/2022 | Waterbury et al. |
| 11,259,870 B2 | 3/2022 | DiMaio et al. |
| 11,259,884 B2 | 3/2022 | Burbank |
| 11,272,993 B2 | 3/2022 | Gomez et al. |
| 11,272,994 B2 | 3/2022 | Saraliev et al. |
| 11,291,442 B2 | 4/2022 | Wixey et al. |
| 11,291,513 B2 | 4/2022 | Manzo et al. |
| 11,529,203 B2 * | 12/2022 | Kopp .................... A61B 34/30 |
| 2001/0031975 A1 | 10/2001 | Whitman |
| 2002/0049454 A1 | 4/2002 | Whitman et al. |
| 2002/0165541 A1 | 11/2002 | Whitman |
| 2003/0038938 A1 | 2/2003 | Jung et al. |
| 2003/0165794 A1 | 9/2003 | Matoba |
| 2004/0034369 A1 | 2/2004 | Sauer et al. |
| 2004/0111012 A1 | 6/2004 | Whitman |
| 2004/0133189 A1 | 7/2004 | Sakurai |
| 2004/0153124 A1 | 8/2004 | Whitman |
| 2004/0176751 A1 | 9/2004 | Weitzner et al. |
| 2004/0193146 A1 | 9/2004 | Lee et al. |
| 2004/0267254 A1 | 12/2004 | Manzo et al. |
| 2005/0125027 A1 | 6/2005 | Knodel et al. |
| 2005/0131442 A1 | 6/2005 | Yachia et al. |
| 2006/0074415 A1 | 4/2006 | Scott et al. |
| 2006/0142656 A1 | 6/2006 | Malackowski et al. |
| 2006/0142740 A1 | 6/2006 | Sherman et al. |
| 2006/0142744 A1 | 6/2006 | Boutoussov |
| 2006/0259073 A1 | 11/2006 | Miyamoto et al. |
| 2006/0278680 A1 | 12/2006 | Viola |
| 2006/0284730 A1 | 12/2006 | Schmid et al. |
| 2007/0023476 A1 | 2/2007 | Whitman et al. |
| 2007/0023477 A1 | 2/2007 | Whitman et al. |
| 2007/0027469 A1 | 2/2007 | Smith et al. |
| 2007/0029363 A1 | 2/2007 | Popov |
| 2007/0084897 A1 | 4/2007 | Shelton et al. |
| 2007/0102472 A1 | 5/2007 | Shelton |
| 2007/0152014 A1 | 7/2007 | Gillum et al. |
| 2007/0175947 A1 | 8/2007 | Ortiz et al. |
| 2007/0175949 A1 | 8/2007 | Shelton et al. |
| 2007/0175950 A1 | 8/2007 | Shelton, IV et al. |
| 2007/0175951 A1 | 8/2007 | Shelton et al. |
| 2007/0175955 A1 | 8/2007 | Shelton et al. |
| 2007/0270784 A1 | 11/2007 | Smith et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0058801 A1 | 3/2008 | Taylor et al. |
| 2008/0109012 A1 | 5/2008 | Falco et al. |
| 2008/0110958 A1 | 5/2008 | McKenna et al. |
| 2008/0147089 A1 | 6/2008 | Loh et al. |
| 2008/0167736 A1 | 7/2008 | Swayze et al. |
| 2008/0179374 A1 * | 7/2008 | Beardsley ........ A61B 17/07207 227/176.1 |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0237296 A1 | 10/2008 | Boudreaux et al. |
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0272172 A1 | 11/2008 | Zemlok et al. |
| 2008/0308603 A1 | 12/2008 | Shelton et al. |
| 2009/0012533 A1 | 1/2009 | Barbagli et al. |
| 2009/0030428 A1 | 1/2009 | Omori et al. |
| 2009/0057370 A1 | 3/2009 | Marczyk et al. |
| 2009/0090763 A1 * | 4/2009 | Zemlok ............ A61B 17/07207 227/175.2 |
| 2009/0099876 A1 | 4/2009 | Whitman |
| 2009/0138006 A1 | 5/2009 | Bales et al. |
| 2009/0171147 A1 | 7/2009 | Lee et al. |
| 2009/0182193 A1 | 7/2009 | Whitman et al. |
| 2009/0209946 A1 | 8/2009 | Swayze et al. |
| 2009/0209990 A1 | 8/2009 | Yates et al. |
| 2009/0254094 A1 | 10/2009 | Knapp et al. |
| 2009/0299141 A1 | 12/2009 | Downey et al. |
| 2010/0023022 A1 | 1/2010 | Zeiner et al. |
| 2010/0069942 A1 | 3/2010 | Shelton, IV |
| 2010/0096432 A1 | 4/2010 | Scirica |
| 2010/0193568 A1 | 8/2010 | Scheib et al. |
| 2010/0211053 A1 | 8/2010 | Ross et al. |
| 2010/0225073 A1 | 9/2010 | Porter et al. |
| 2011/0006101 A1 | 1/2011 | Hall et al. |
| 2011/0017801 A1 | 1/2011 | Zemlok et al. |
| 2011/0071508 A1 | 3/2011 | Duval et al. |
| 2011/0077673 A1 | 3/2011 | Grubac et al. |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0155783 A1 | 6/2011 | Rajappa et al. |
| 2011/0155786 A1 | 6/2011 | Shelton, IV |
| 2011/0172648 A1 | 7/2011 | Jeong |
| 2011/0174009 A1 | 7/2011 | Iizuka et al. |
| 2011/0174099 A1 * | 7/2011 | Ross ...................... A61B 17/00 74/89.32 |
| 2011/0184245 A1 | 7/2011 | Xia et al. |
| 2011/0204119 A1 | 8/2011 | McCuen |
| 2011/0218522 A1 | 9/2011 | Whitman |
| 2011/0276057 A1 | 11/2011 | Conlon et al. |
| 2011/0290854 A1 | 12/2011 | Timm et al. |
| 2011/0295242 A1 | 12/2011 | Spivey et al. |
| 2011/0295269 A1 | 12/2011 | Swensgard et al. |
| 2012/0000962 A1 | 1/2012 | Racenet et al. |
| 2012/0074199 A1 | 3/2012 | Olson et al. |
| 2012/0089131 A1 | 4/2012 | Zemlok et al. |

(56) References Cited

U.S. PATENT DOCUMENTS

| | | |
|---|---|---|
| 2012/0104071 A1 | 5/2012 | Bryant |
| 2012/0116368 A1 | 5/2012 | Viola |
| 2012/0116416 A1 | 5/2012 | Neff et al. |
| 2012/0143002 A1 | 6/2012 | Aranyi et al. |
| 2012/0172924 A1 | 7/2012 | Allen, IV |
| 2012/0211542 A1 | 8/2012 | Racenet |
| 2012/0223121 A1 | 9/2012 | Viola et al. |
| 2012/0245428 A1 | 9/2012 | Smith et al. |
| 2012/0253329 A1 | 10/2012 | Zemlok et al. |
| 2012/0259338 A1 | 10/2012 | Carr et al. |
| 2012/0310220 A1 | 12/2012 | Malkowski et al. |
| 2012/0323226 A1 | 12/2012 | Chowaniec et al. |
| 2012/0330285 A1 | 12/2012 | Hartoumbekis et al. |
| 2013/0093149 A1 | 4/2013 | Saur et al. |
| 2013/0138129 A1 | 5/2013 | Garrison et al. |
| 2013/0181035 A1 | 7/2013 | Milliman |
| 2013/0184704 A1 | 7/2013 | Beardsley et al. |
| 2013/0214025 A1 | 8/2013 | Zemlok et al. |
| 2013/0274722 A1 | 10/2013 | Kostrzewski et al. |
| 2013/0282052 A1 | 10/2013 | Aranyi et al. |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |
| 2013/0319706 A1 | 12/2013 | Nicholas et al. |
| 2013/0324978 A1 | 12/2013 | Nicholas et al. |
| 2013/0324979 A1 | 12/2013 | Nicholas et al. |
| 2013/0334281 A1 | 12/2013 | Williams |
| 2014/0001234 A1* | 1/2014 | Shelton, IV ......... A61B 17/068 74/25 |
| 2014/0001235 A1 | 1/2014 | Shelton, IV |
| 2014/0012236 A1 | 1/2014 | Williams et al. |
| 2014/0012237 A1 | 1/2014 | Pribanic et al. |
| 2014/0012289 A1* | 1/2014 | Snow ................ A61B 17/068 606/130 |
| 2014/0025046 A1 | 1/2014 | Williams et al. |
| 2014/0110455 A1 | 4/2014 | Ingmanson et al. |
| 2014/0207125 A1 | 7/2014 | Applegate et al. |
| 2014/0207182 A1* | 7/2014 | Zergiebel ......... A61B 17/07207 606/205 |
| 2014/0207185 A1 | 7/2014 | Goble et al. |
| 2014/0236174 A1 | 8/2014 | Williams et al. |
| 2014/0276932 A1 | 9/2014 | Williams et al. |
| 2014/0277334 A1* | 9/2014 | Yu ........................ A61B 34/30 901/30 |
| 2014/0299647 A1 | 10/2014 | Scirica et al. |
| 2014/0303668 A1 | 10/2014 | Nicholas et al. |
| 2014/0305987 A1 | 10/2014 | Parihar |
| 2014/0305990 A1 | 10/2014 | Shelton, IV et al. |
| 2014/0358129 A1 | 12/2014 | Zergiebel et al. |
| 2014/0361068 A1 | 12/2014 | Aranyi et al. |
| 2014/0365235 A1 | 12/2014 | DeBoer et al. |
| 2014/0373652 A1 | 12/2014 | Zergiebel et al. |
| 2015/0014392 A1 | 1/2015 | Williams et al. |
| 2015/0048144 A1 | 2/2015 | Whitman |
| 2015/0076205 A1 | 3/2015 | Zergiebel |
| 2015/0080912 A1 | 3/2015 | Sapre |
| 2015/0112381 A1 | 4/2015 | Richard |
| 2015/0122870 A1 | 5/2015 | Zemlok et al. |
| 2015/0133224 A1 | 5/2015 | Whitman et al. |
| 2015/0150547 A1 | 6/2015 | Ingmanson et al. |
| 2015/0150574 A1 | 6/2015 | Richard et al. |
| 2015/0157320 A1 | 6/2015 | Zergiebel et al. |
| 2015/0157321 A1 | 6/2015 | Zergiebel et al. |
| 2015/0164502 A1 | 6/2015 | Richard et al. |
| 2015/0201931 A1 | 7/2015 | Zergiebel et al. |
| 2015/0272577 A1 | 10/2015 | Zemlok et al. |
| 2015/0297199 A1 | 10/2015 | Nicholas et al. |
| 2015/0303996 A1 | 10/2015 | Calderoni |
| 2015/0320420 A1 | 11/2015 | Penna et al. |
| 2015/0327850 A1 | 11/2015 | Kostrzewski |
| 2015/0342601 A1 | 12/2015 | Williams et al. |
| 2015/0342603 A1 | 12/2015 | Zergiebel et al. |
| 2015/0374366 A1 | 12/2015 | Zergiebel et al. |
| 2015/0374370 A1 | 12/2015 | Zergiebel et al. |
| 2015/0374371 A1 | 12/2015 | Richard et al. |
| 2015/0374372 A1 | 12/2015 | Zergiebel et al. |
| 2015/0374449 A1 | 12/2015 | Chowaniec et al. |
| 2015/0380187 A1 | 12/2015 | Zergiebel et al. |
| 2016/0095585 A1 | 4/2016 | Zergiebel et al. |
| 2016/0095596 A1 | 4/2016 | Scirica et al. |
| 2016/0106406 A1 | 4/2016 | Cabrera |
| 2016/0113648 A1 | 4/2016 | Zergiebel et al. |
| 2016/0113649 A1 | 4/2016 | Zergiebel et al. |
| 2016/0174969 A1 | 6/2016 | Kerr |
| 2018/0243035 A1 | 8/2018 | Kopp |

FOREIGN PATENT DOCUMENTS

| | | |
|---|---|---|
| CN | 1957854 A | 5/2007 |
| CN | 101495046 A | 7/2009 |
| CN | 101856251 A | 10/2010 |
| CN | 102247182 A | 11/2011 |
| DE | 102008053842 A1 | 5/2010 |
| EP | 0705571 A1 | 4/1996 |
| EP | 1563793 A1 | 8/2005 |
| EP | 1759652 A2 | 3/2007 |
| EP | 1769754 A1 | 4/2007 |
| EP | 1908412 A2 | 4/2008 |
| EP | 1917929 A1 | 5/2008 |
| EP | 1952769 A2 | 8/2008 |
| EP | 2030577 A2 | 3/2009 |
| EP | 2090247 A1 | 8/2009 |
| EP | 2245994 A1 | 11/2010 |
| EP | 2316345 A1 | 5/2011 |
| EP | 2377472 A1 | 10/2011 |
| EP | 2668910 A2 | 12/2013 |
| EP | 2792306 A2 | 10/2014 |
| EP | 2815705 A1 | 12/2014 |
| ES | 2333509 A1 | 2/2010 |
| FR | 2861574 A1 | 5/2005 |
| JP | 2005125075 A | 5/2005 |
| JP | 2007054642 A | 3/2007 |
| JP | 2011206213 A | 10/2011 |
| JP | 2014513570 A | 6/2014 |
| JP | 2015524286 A | 8/2015 |
| JP | 2018532465 A | 11/2018 |
| KR | 20120022521 A | 3/2012 |
| WO | 2011108840 A2 | 9/2011 |
| WO | 2012040984 A1 | 4/2012 |

OTHER PUBLICATIONS

Extended European Search Report corresponding to International Application No. EP 14 18 4882.0 dated May 12, 2015.
Canadian Office Action corresponding to International Application No. CA 2640399 dated May 7, 2015.
Japanese Office Action corresponding to International Application No. JP 2011-197365 dated Mar. 23, 2015.
Japanese Office Action corresponding to International Application No. JP 2011-084092 dated May 20, 2015.
Japanese Office Action corresponding to International Application No. JP 2014-148482 dated Jun. 2, 2015.
Extended European Search Report corresponding to International Application No. EP 14 18 9358.6 dated Jul. 8, 2015.
Extended European Search Report corresponding to International Application No. EP 14 19 6148.2 dated Apr. 23, 2015.
Partial European Search Report corresponding to International Application No. EP 14 19 6704.2 dated May 11, 2015.
Australian Office Action corresponding to International Application No. AU 2010241367 dated Aug. 20, 2015.
Partial European Search Report corresponding to International Application No. EP 14 19 9783.3 dated Sep. 3, 2015.
Extended European Search Report corresponding to International Application No. EP 15 16 9962.6 dated Sep. 14, 2015.
Extended European Search Report corresponding to International Application No. EP 15 15 1076.5 dated Apr. 22, 2015.
Japanese Office Action corresponding to International Application No. JP 2011-084092 dated Jan. 14, 2016.
Extended European Search Report corresponding to International Application No. EP 12 19 7970.2 dated Jan. 28, 2016.

(56) References Cited

OTHER PUBLICATIONS

Chinese Office Action corresponding to International Application No. CN 201210560638.1 dated Oct. 21, 2015.
European Office Action corresponding to International Application No. EP 14 15 9056.2 dated Oct. 26, 2015.
Australian Examination Report No. 1 corresponding to International Application No. AU 2015200153 dated Dec. 11, 2015.
Australian Examination Report No. 1 corresponding to International Application No. AU 2014204542 dated Jan. 7, 2016.
Chinese Office Action corresponding to International Application No. CN 201310125449.6 dated Feb. 3, 2016.
Extended European Search Report corresponding to International Application No. EP 15 19 0245.9 dated Jan. 28, 2016.
Extended European Search Report corresponding to International Application No. EP 15 16 7793.7 dated Apr. 5, 2016.
European Office Action corresponding to International Application No. EP 14 18 4882.0 dated Apr. 25, 2016.
Extended European Search Report corresponding to International Application No. EP 14 19 6704.2 dated Sep. 24, 2015.
International Search Report and Written Opinion corresponding to Int'l Appln. No. PCT/US2015/051837, dated Dec. 21, 2015.
Extended European Search Report corresponding to International Application No. EP 14 19 7563.1 dated Aug. 5, 2015.
Partial European Search Report corresponding to International Application No. EP 15 19 0643.5 dated Feb. 26, 2016.
Extended European Search Report corresponding to International Application No. EP 15 16 6899.3 dated Feb. 3, 2016.
Extended European Search Report corresponding to International Application No. EP 14 19 9783.3 dated Dec. 22, 2015.
Extended European Search Report corresponding to International Application No. EP 15 17 3807.7 dated Nov. 24, 2015.
Extended European Search Report corresponding to International Application No. EP 15 19 0760.7 dated Apr. 1, 2016.
Extended European Search Report corresponding to International Application No. EP 15 17 3803.6 dated Nov. 24, 2015.
Extended European Search Report corresponding to International Application No. EP 15 17 3804.4 dated Nov. 24, 2015.
Extended European Search Report corresponding to International Application No. EP 15 18 8539.9 dated Feb. 17, 2016.
Extended European Search Report corresponding to International Application No. EP 15 17 3910.9 dated Nov. 13, 2015.
European Office Action corresponding to International Application No. EP 14 15 2236.7 dated Aug. 11, 2015.
Extended European Search Report corresponding to International Application No. EP 15 18 4915.5 dated Jan. 5, 2016.
Chinese Office Action corresponding to counterpart Int'l Appln. No. CN 201310369318.2 dated Jun. 28, 2016.
Chinese Office Action (with English translation), dated Jul. 4, 2016, corresponding to Chinese Patent Application No. 2015101559718; 23 total pages.
European Search Report EP 15 156 035.6 dated Aug. 10, 2016.
European Search Report corresponding to EP 15 184 915.-1654 dated Sep. 16, 2016.
Australian Examination Report No. 1 corresponding to International Application No. AU 2013205872 dated Oct. 19, 2016.
Australian Examination Report from Appl. No. AU 2013205840 dated Nov. 3, 2016.
Extended European Search Report dated Jun. 12, 2019 corresponding to counterpart Patent Application EP 16849463.1.
Japanese Notice of Allowance corresponding to counterpart Patent Application No. JP 2018-515023 dated Jul. 21, 2020.
Japanese Office Action dated Jun. 29, 2021 corresponding to counterpart Patent Application JP 2020-141545.
Australian Examination Report No. 1 dated Feb. 16, 2021 corresponding to counterpart Patent Application AU 2020239641.
Extended European Search Report issued in corresponding application 23186047.9 dated Feb. 15, 2024 (13 pages).

* cited by examiner

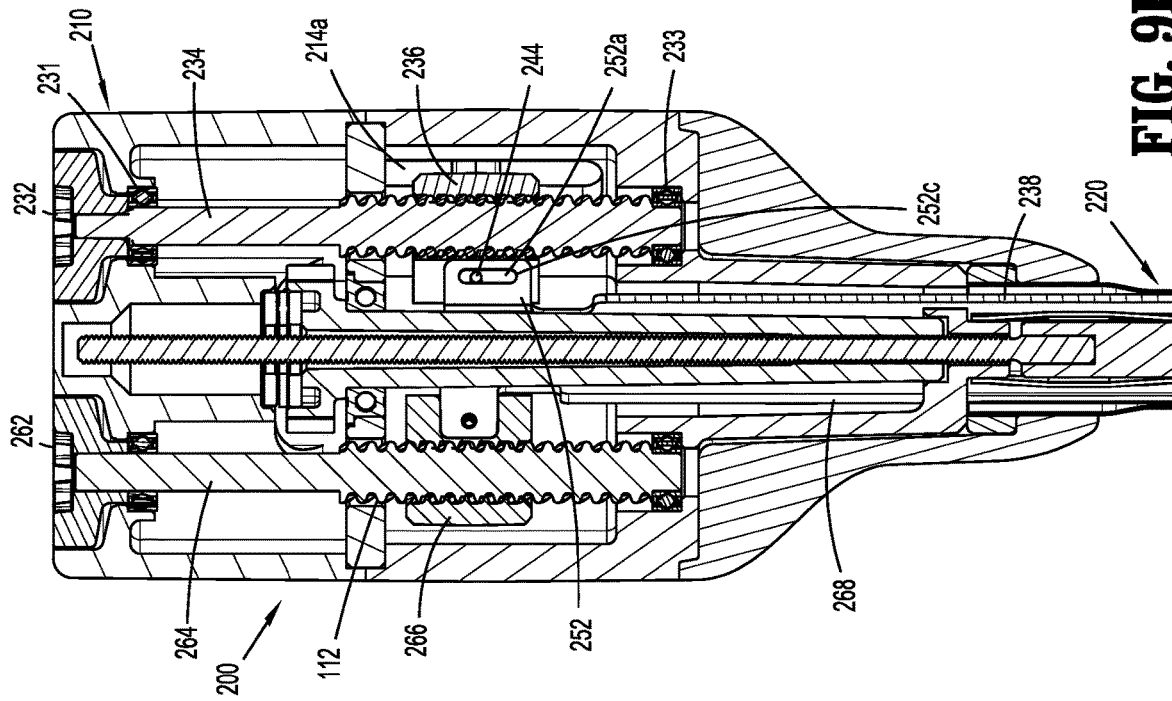
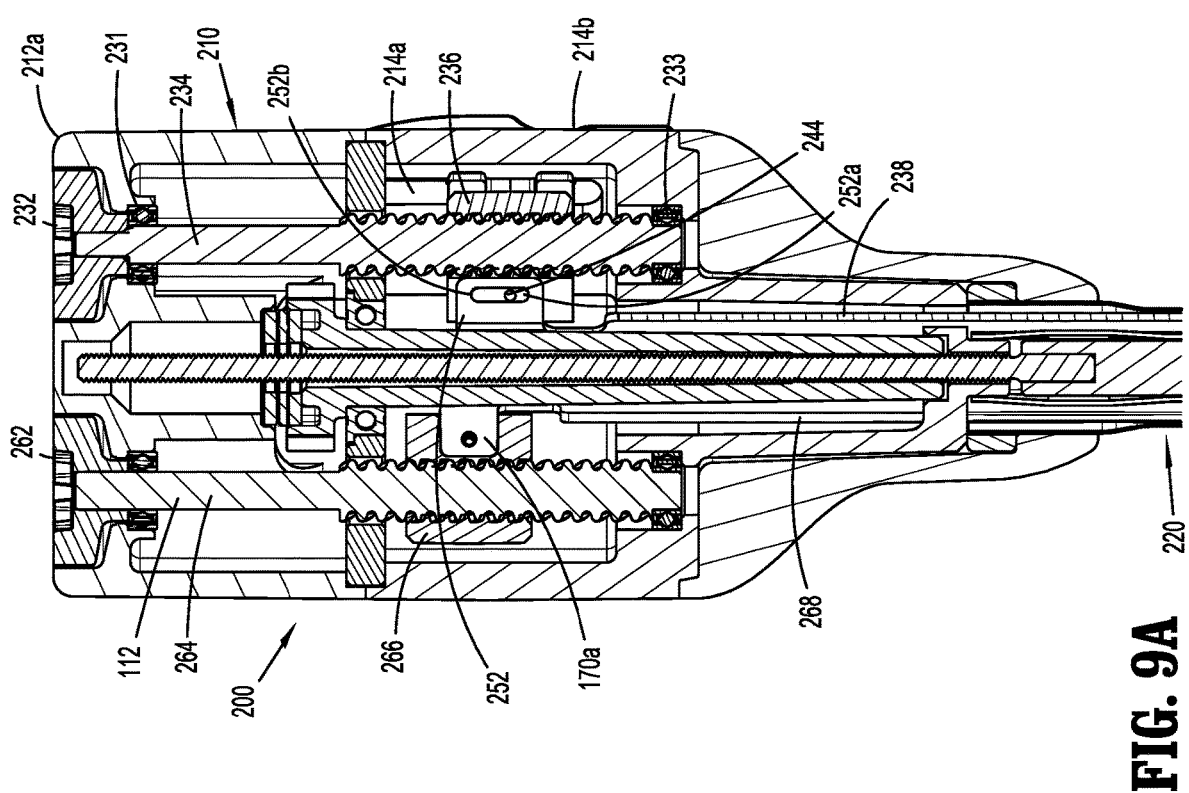
FIG. 9A
FIG. 9B

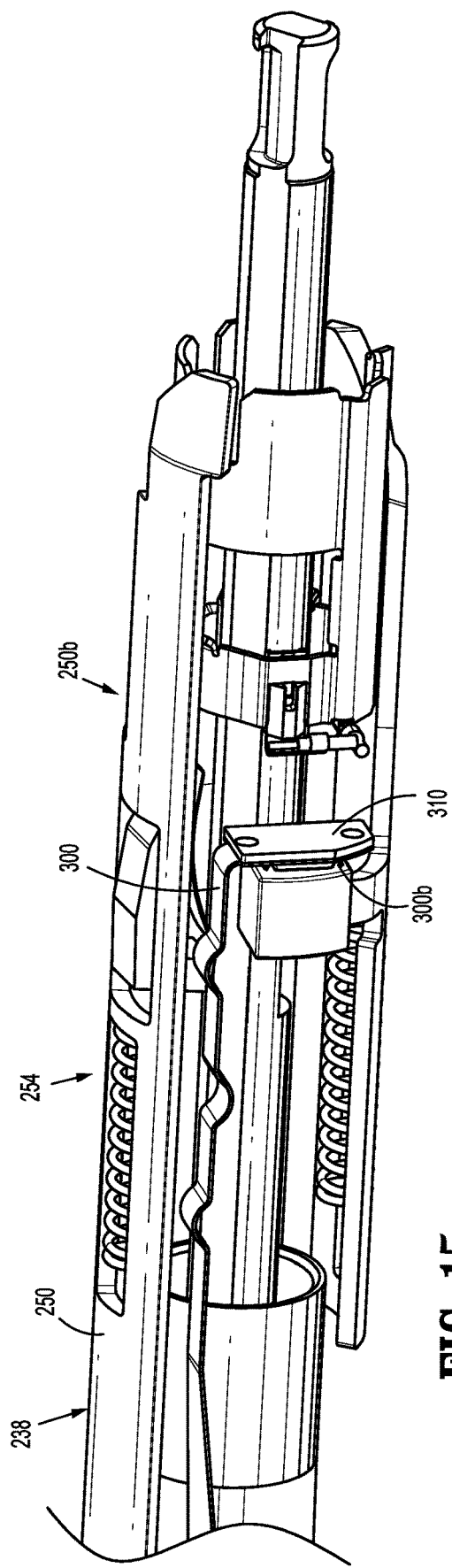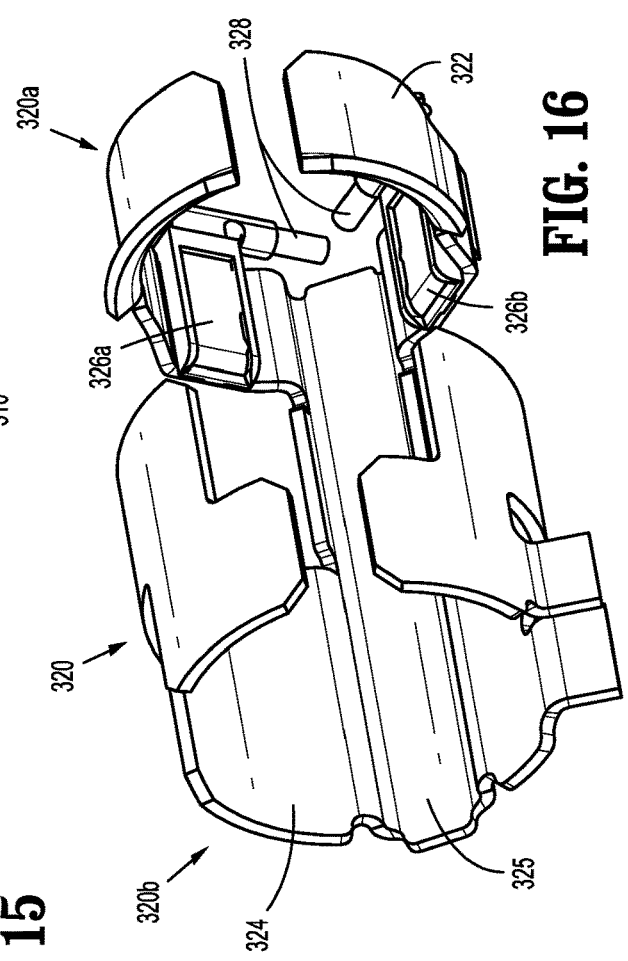

ROBOTIC SURGICAL ASSEMBLIES AND INSTRUMENT DRIVE CONNECTORS THEREOF

CROSS-REFERENCE TO RELATED APPLICATIONS

This application is a continuation of U.S. patent application Ser. No. 17/024,925, filed Sep. 18, 2020, now U.S. Pat. No. 11,529,203, which is a continuation of U.S. patent application Ser. No. 15/758,986, filed Mar. 9, 2018, now U.S. Pat. No. 10,806,454, which is a U.S. National Stage Application filed under 35 U.S.C. § 371 of International Patent Application Serial No. PCT/US2016/052783, filed Sep. 21, 2016, which claims the benefit of and priority to U.S. Provisional Patent Application Ser. No. 62/232,640, filed Sep. 25, 2015. The entire disclosures of each of the foregoing applications are incorporated by reference herein.

BACKGROUND

Robotic surgical systems have been used in minimally invasive medical procedures. Some robotic surgical systems included a console supporting a robot arm and a surgical instrument, having at least one end effector (e.g., a forceps or a grasping tool), mounted to the robot arm. The robotic arm provided mechanical power to the surgical instrument for its operation and movement.

Robotic surgical systems supported surgical instruments that were configured to couple to a variety of types of end effectors by enabling these end effectors to be readily exchanged during a surgical procedure. Typically, this exchange of end effectors was performed by manually detaching the end effector from the remainder of the surgical instrument without detaching the instrument drive unit from the surgical instrument. This often meant that end effectors could be detached from the surgical instrument by a clinician inadvertently by hitting the wrong button or switch.

SUMMARY

The present disclosure is directed to surgical instruments having an instrument drive connector that is releasably coupled to an end effector and that reduces the likelihood of inadvertent removal of the end effector from a surgical instrument during the end effector exchange process.

In one aspect of the present disclosure, an instrument drive connector for interconnecting an instrument drive unit and an end effector, wherein the instrument drive connector transmits at least one force from the instrument drive unit to the end effector to effect a function of the end effector, includes a housing assembly, an elongated shaft extending distally from the housing assembly, and a first drive assembly at least partially disposed within the housing assembly and the elongated shaft. The first drive assembly includes a first drive screw having a proximal end and a distal end, a first input drive coupler non-rotatably coupled to the proximal end of the first drive screw, a first drive nut threadedly engaged with a threaded body portion of the first drive screw and longitudinally movable relative thereto in response to rotation of the first drive screw, and a locking link. The locking link includes an elongated body having a proximal end portion and a distal end portion, the proximal end portion is coupled to the first drive nut and longitudinally movable relative thereto between a proximal non-locking position and a distal locking position, and the distal end portion includes a switch actuation assembly including a switch actuating arm biased towards the distal locking position.

In embodiments, the switch actuation assembly includes a coil spring disposed in an elongated opening proximal of the switch actuating arm. The coil spring biases the switch actuating arm towards the distal locking position and is movable to the proximal non-locking position.

The instrument drive connector may include a switch disposed in the elongated shaft. In some embodiments, the instrument drive connector includes an annular member disposed in a distal end of the elongated shaft. The annular member may include a pair of electrical contacts electrically coupled to the switch.

A flex circuit may be disposed in the elongated shaft, and the switch may be disposed at a distal end of the flex circuit. In some embodiments, the flex circuit extends longitudinally through the elongated shaft, and includes a proximal end configured for electrical communication with a processor.

The proximal end portion of the locking link may include a longitudinal slot formed therein, and the first drive nut may have a rod disposed within the longitudinal slot of the locking link such that when the first drive nut is in the distal locking position, the rod of the first drive nut is engaged with a distal end surface of the longitudinal slot, and when the first drive nut is in the proximal non-locking position, the rod of the first drive nut is disposed adjacent a proximal end surface of the longitudinal slot.

In embodiments, the housing assembly defines an aperture in a side surface thereof, and the first drive nut includes a tab extending through the aperture and into a finger switch for manual movement of the first drive nut.

The instrument drive connector may include a second drive assembly. The second drive assembly may include a second drive screw having a proximal end and a distal end, a second input drive coupler non-rotatably coupled to the proximal end of the second drive screw, a second drive nut threadedly engaged with a threaded body portion of the second drive screw and longitudinally movable relative thereto in response to rotation of the second drive screw, and an articulation link. The articulation link may include an elongated body having a proximal end and a distal end, the proximal end fixedly coupled to the second drive nut such that longitudinal translation of the second drive nut causes longitudinal translation of the articulation link.

The instrument drive connector may include a third drive assembly. The third drive assembly may include a proximal shaft, a distal shaft, a drive rod, and a drive shaft. The proximal shaft may include a third input drive coupler non-rotatably secured to a proximal end of the proximal shaft and a distal gear non-rotatably secured to a distal end of the proximal shaft. The distal shaft may include a proximal gear non-rotatably secured thereto and meshingly engaged with the distal gear of the proximal shaft. The drive rod may include a threaded elongated body engaged with a threaded channel defined in the distal shaft and is longitudinally movable relative thereto in response to rotation of the distal shaft. The drive shaft may be coupled to a distal end of the drive rod and may be longitudinally movable therewith.

In another aspect of the present disclosure, a surgical instrument for use with and for selective connection to an instrument drive unit, includes an instrument drive connector and a surgical loading unit. The instrument drive connector includes a housing assembly and an elongated shaft, and a first drive assembly at least partially disposed within the housing assembly and the elongated shaft. The first drive assembly includes a first drive screw having a proximal end and a distal end, a first input drive coupler non-rotatably coupled to the proximal end of the first drive screw, a first drive nut threadedly engaged with a threaded body portion of the first drive screw and longitudinally movable relative thereto in response to rotation of the first drive screw, and a locking link. The locking link includes an elongated body having a proximal end portion and a distal end portion, the proximal end portion is coupled to the first drive nut and longitudinally movable relative thereto between a proximal non-locking position and a distal locking position, and the distal end portion includes a switch actuation assembly including a switch actuating arm biased towards the distal locking position. The surgical loading unit is selectively attachable to the instrument drive connector and includes an end effector. When the locking link of the first drive assembly is in the proximal non-locking position, the surgical loading unit can be inserted or removed from the instrument drive connector, and when the locking link is in the distal locking position, the surgical loading unit cannot be either inserted or removed from instrument drive connector.

In embodiments, the switch actuation assembly of the locking link of the first drive assembly includes a coil spring disposed in an elongated opening proximal of the switch actuating arm. The coil spring biases the switch actuating arm towards the distal locking position and is movable to the proximal non-locking position.

The instrument drive connector may include a switch disposed in the elongated shaft. In some embodiments, the instrument drive connector includes an annular member disposed in a distal end of the elongated shaft. The annular member may include a pair of electrical contacts electrically coupled to the switch.

The instrument drive connector may include a flex circuit disposed in the elongated shaft, and the switch may be disposed at a distal end of the flex circuit. In some embodiments, the flex circuit extends longitudinally through the elongated shaft of the instrument drive connector, and includes a proximal end configured for electrical communication with a processor.

The proximal end portion of the locking link may include a longitudinal slot formed therein, and the first drive nut may have a rod disposed within the longitudinal slot of the locking link such that when the first drive nut is in the distal locking position, the rod of the first drive nut is engaged with a distal end surface of the longitudinal slot, and when the first drive nut is in the proximal non-locking position, the rod of the first drive nut is disposed adjacent a proximal end surface of the longitudinal slot.

In embodiments, the housing assembly of the instrument drive connector defines an aperture in a side surface thereof, and the first drive nut includes a tab extending through the aperture and into a finger switch for manual movement of the first drive nut.

The instrument drive connector may include a second drive assembly. The second drive assembly may include a second drive screw having a proximal end and a distal end, a second input drive coupler non-rotatably coupled to the proximal end of the second drive screw, a second drive nut threadedly engaged with a threaded body portion of the second drive screw and longitudinally movable relative thereto in response to rotation of the second drive screw, and an articulation link. The articulation link may include an elongated body having a proximal end and a distal end, the proximal end fixedly coupled to the second drive nut such that longitudinal translation of the second drive nut causes longitudinal translation of the articulation link. The distal end of the articulation link may be releasably coupled to the surgical loading unit to effect articulation of the end effector.

The instrument drive connector may include a third drive assembly including a proximal shaft, a distal shaft, a drive rod, and a drive shaft. The proximal shaft may include a third input drive coupler non-rotatably secured to a proximal end of the proximal shaft and a distal gear non-rotatably secured to a distal end of the proximal shaft. The distal shaft may include a proximal gear non-rotatably secured thereto and meshingly engaged with the distal gear of the proximal shaft. The drive rod may include a threaded elongated body engaged with a threaded channel defined in the distal shaft and longitudinally movable relative thereto in response to rotation of the distal shaft. The drive shaft may be coupled to a distal end of the drive rod and is longitudinally movable therewith. A distal end of the drive shaft may be in operable communication with the surgical loading unit to affect a function of the end effector.

Other aspects, features, and advantages will be apparent from the description, the drawings, and the claims.

BRIEF DESCRIPTION OF THE DRAWINGS

The accompanying drawings, which are incorporated in and constitute a part of this specification, and in which corresponding reference characters indicate corresponding parts in each of the several views, illustrate embodiments of the disclosure and, together with a general description of the disclosure given above, and the detailed description of the embodiment(s) given below, serve to explain the principles of the disclosure, wherein:

FIG. 9A is a cross-sectional view of the instrument drive connector of FIGS. 3-8, taken along line 6-6 of FIG. 5, illustrating a first drive nut of the instrument drive connector in a locking position;

FIG. 9B is a cross-sectional view of the instrument drive connector of FIGS. 3-9A, taken along line 6-6 of FIG. 5, illustrating a first drive nut of the instrument drive connector in a non-locking position;

FIG. 15 is an enlarged perspective view, with parts removed, of the internal components of the instrument drive connector of FIG. 14; and FIG. 16 is a perspective view of an annular member of instrument drive connector of FIG. 15.

DETAILED DESCRIPTION

In this disclosure, the term "distal" refers to a portion of a structure that is farther from a clinician, while the term "proximal" refers to a portion of the same structure that is closer to the clinician. As used herein, the term "subject" refers to a human patient or other animal. The term "clinician" refers to a doctor (e.g., a surgeon), nurse, or other care provider, and may include support personnel.

Figure 1:
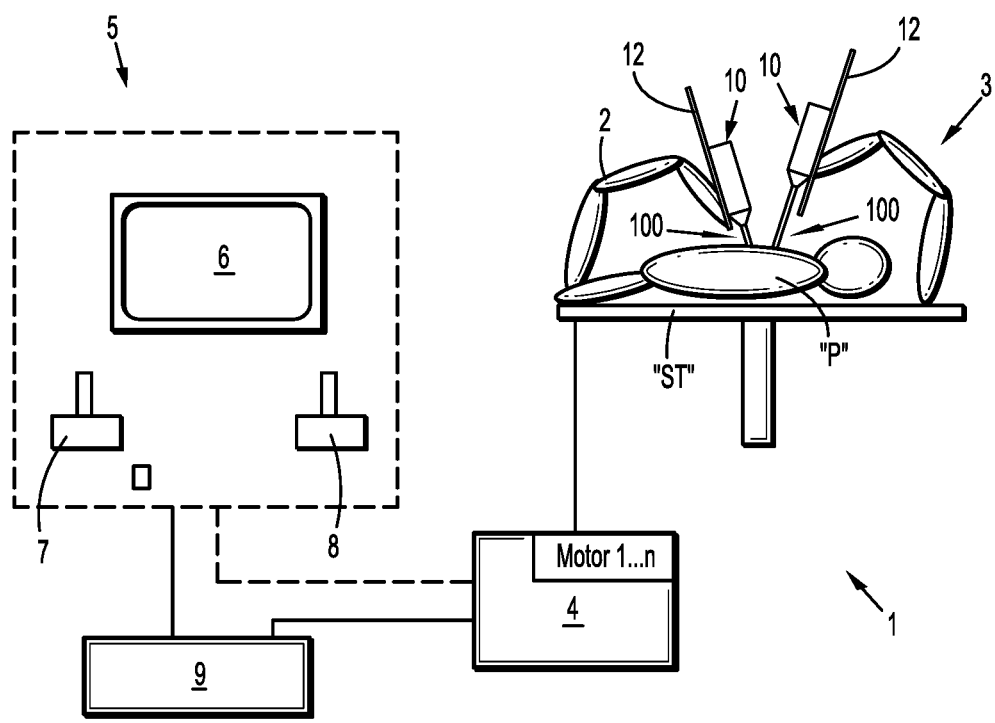
FIG. 1 is a schematic illustration of a robotic surgical system in accordance with the present disclosure.

Referring initially to FIG. 1, a robotic surgical system, such as, for example, medical work station 1, generally includes a plurality of robot arms 2 and 3, a control device 4, and an operating console 5 coupled with control device 4. Operating console 5 includes a display device 6, which is set up in particular to display three-dimensional images, and manual input devices 7 and 8, by means of which a clinician (not shown), for example a surgeon, is able to telemanipulate robot arms 2 and 3 in a first operating mode, as known in principle to a person skilled in the art.

Each of the robot arms 2 and 3 includes a plurality of members, which are connected through joints, to which may be releasably attached, for example, a surgical assembly 10. Robot arms 2 and 3 may be driven by electric drives (not shown) that are connected to control device 4. Control device 4 (e.g., a computer) is set up to activate the drives, in particular by means of a computer program, in such a way that robot arms 2 and 3 and/or surgical assembly 10 execute a desired movement according to a movement defined by means of manual input devices 7 and 8. Control device 4 may also be set up in such a way that it regulates the movement of robot arms 2 and 3 and/or of the drives (not shown). Control device 4 may control a plurality of motors, e.g., "Motor 1 . . . n," with each motor configured to drive movement of robotic arms 2 and 3 in a plurality of directions.

Medical work station 1 is configured for use on a patient "P" lying on a patient table "ST" to be treated in a minimally invasive manner by means of a surgical instrument 100 of surgical assembly 10. Medical work station 1 may also include more than two robot arms 2 and 3, the additional robot arms likewise being connected to control device 4 and being telemanipulatable by means of operating console 5. A surgical assembly 10, may also be attached to the additional robot arm. Medical work station 1 may include a database 9, in particular coupled to with control device 4, in which are stored for example pre-operative data from patient "P" and/or anatomical atlases.

Reference may be made to U.S. Patent Publication No. 2012/0116416, filed on Nov. 3, 2011, entitled "Medical Workstation," the entire content of which is incorporated herein by reference, for a detailed discussion of the construction and operation of medical work station 1.

Figure 2:
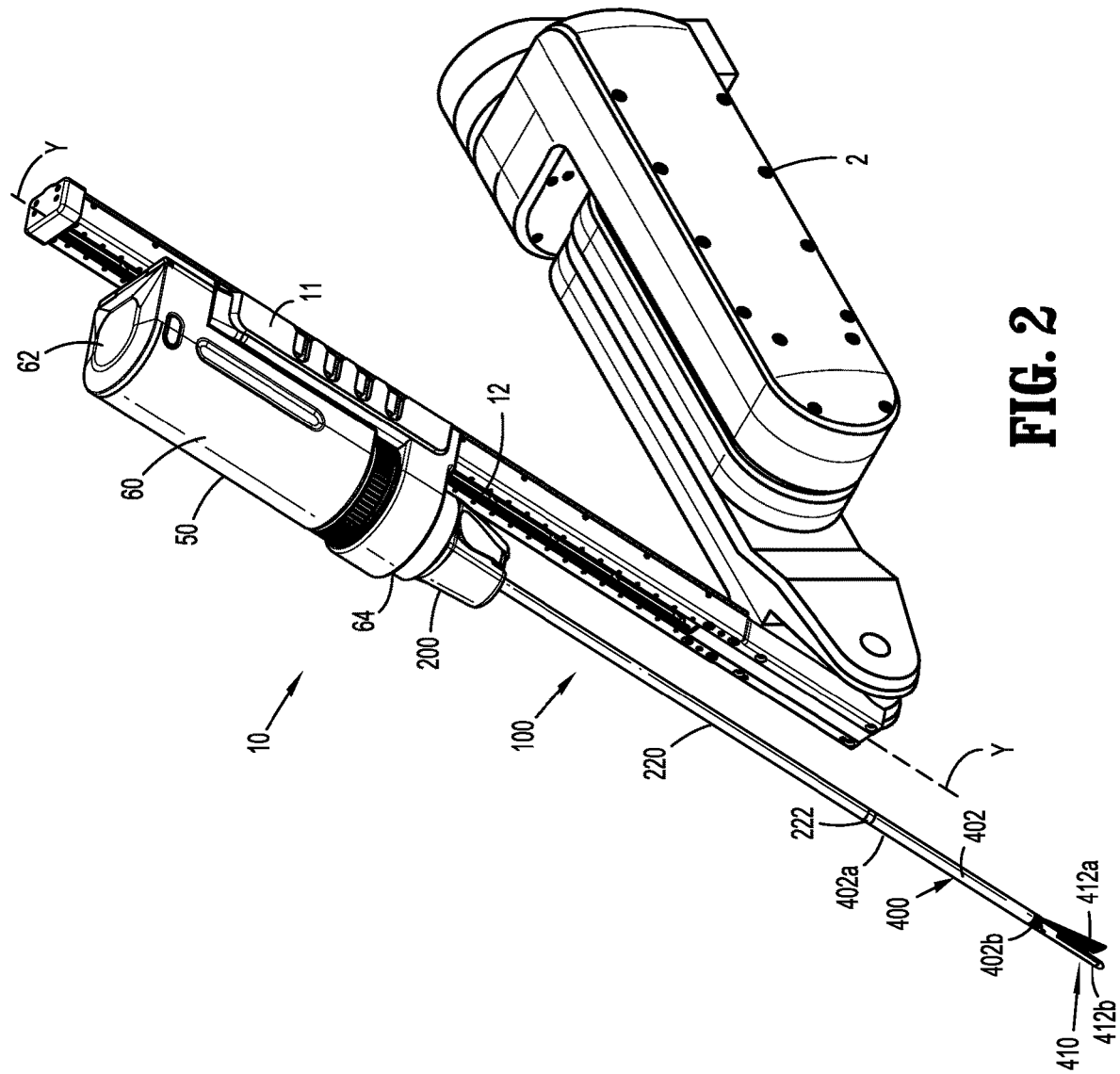
FIG. 2 is a perspective view of a surgical assembly of the robotic surgical system of FIG. 1.

Turning now to FIG. 2, surgical assembly 10 is shown coupled with or to robotic arm 2 via a rail, track, or slide 12. While surgical assembly 10 is discussed singularly, a person of ordinary skill in the art can readily appreciate that the medical work station 1 may also include a plurality of substantially identical surgical assemblies 10 coupled with or to each of the robotic arms 2 and 3 (FIG. 1). Surgical assembly 10 includes an instrument drive unit 50 coupled to an adapter or instrument drive connector 200 of surgical instrument 100 having a surgical loading unit 400 including an end effector 410 disposed at a distal end thereof.

Instrument drive unit 50 of surgical assembly 10 may be supported on or connected to a slider 11 that is movably connected to a track 12 of robotic arm 2. Slider 11 moves, slides, or translates along a longitudinal axis "Y" defined by track 12 of surgical robotic arm 2 upon a selective actuation by motors (not shown) disposed in track 12 of robotic arm 2 or motors (e.g., one or more of "Motor 1 . . . n") of control device 4. As such, slider 11, with surgical assembly 10 connected thereto, can be moved to a selected position along track 12 of robotic arm 2.

Instrument drive unit 50 includes a housing 60 having a proximal end 62 and a distal end 64 configured to be operably coupled to instrument drive connector 200 of surgical instrument 100. Housing 60 of instrument drive unit 50 houses a plurality of motors (not shown) that are configured to power surgical instrument 100, for example, to drive various operations of end effector 410 of surgical instrument 100. Each motor of instrument drive unit 50 includes an output drive coupler (not shown) attached thereto such that the drive couplers are independently rotatable with respect to one another. Drive couplers are disposed at distal end 64 of housing 60 of instrument drive unit 50 and are at least partially exposed for engagement with drive assemblies of instrument drive connector 200. Thus, in use, instrument drive unit 50 transfers power and actuation forces from its motors to instrument drive connector 200 of surgical instrument 100 via rotation of the output drive couplers to ultimately drive movement of components of end effector 410 of surgical instrument 100, as described in further detail below.

Control device 4 (FIG. 1) may control the motors of instrument drive unit 50. In some embodiments, one or more motors may receive signals wirelessly (e.g., from control device 4). It is contemplated that control device 4 coordinates the activation of the various motors ("Motor 1 . . . n"), and the motors of instrument drive unit 50, to coordinate an operation and/or movement of surgical instrument 100.

Surgical loading unit 400 is selectively attachable to instrument drive connector 200 and includes an elongate portion 402 and an end effector 410. Surgical loading unit 400 may be a single use loading unit that is disposable, or a multiple use loading unit that can be sterilized for reuse. Elongate portion 402 of surgical loading unit 400 may be tubular and has a proximal end 402a configured to be coupled to a distal cap 222 of an elongated shaft 220 of instrument drive connector 200. Proximal end 402a of elongate portion 402 has a protrusion or lug (not shown) extending laterally therefrom that is configured to be axially passed through distal cap 222 of elongated shaft 220 of instrument drive connector 200 and rotated to selectively lockingly couple surgical loading unit 400 with instrument drive connector 200. Elongate portion 402 of surgical loading unit 400 has a distal end 402b having end effector 410 attached thereto. End effector 410 generally includes a pair of opposing jaw members 412a and 412b, and may include a staple cartridge, knife blade, among other fastening, cutting, clamping elements within the purview of those skilled in the art. It is contemplated that end effector 410 may be directly coupled to instrument drive connector 200 rather than be directly coupled to elongate portion 402 of surgical loading unit 400.

Figure 3:
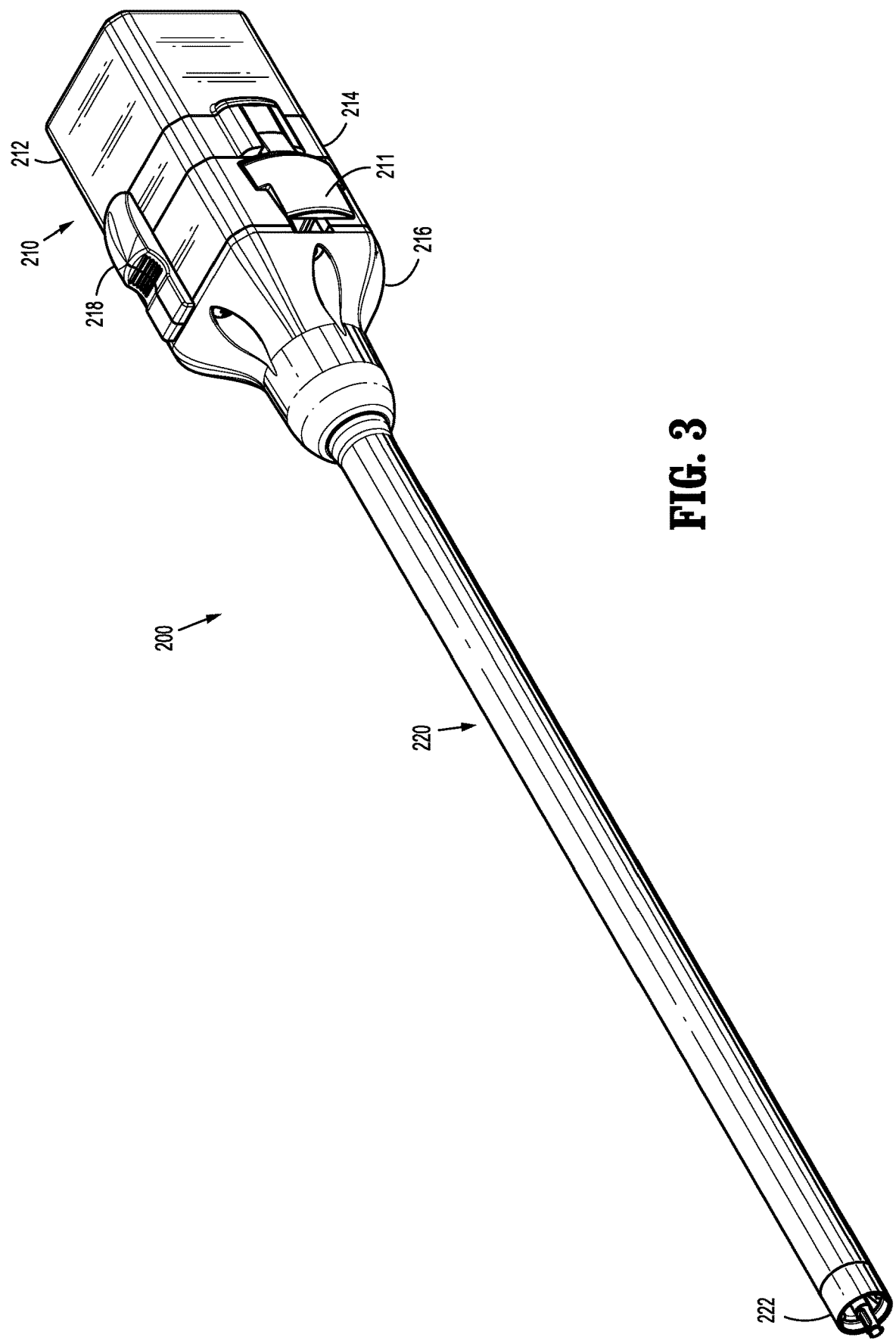
FIG. 3 is a perspective view of an instrument drive connector of the surgical assembly of FIG. 2.
Figure 4:
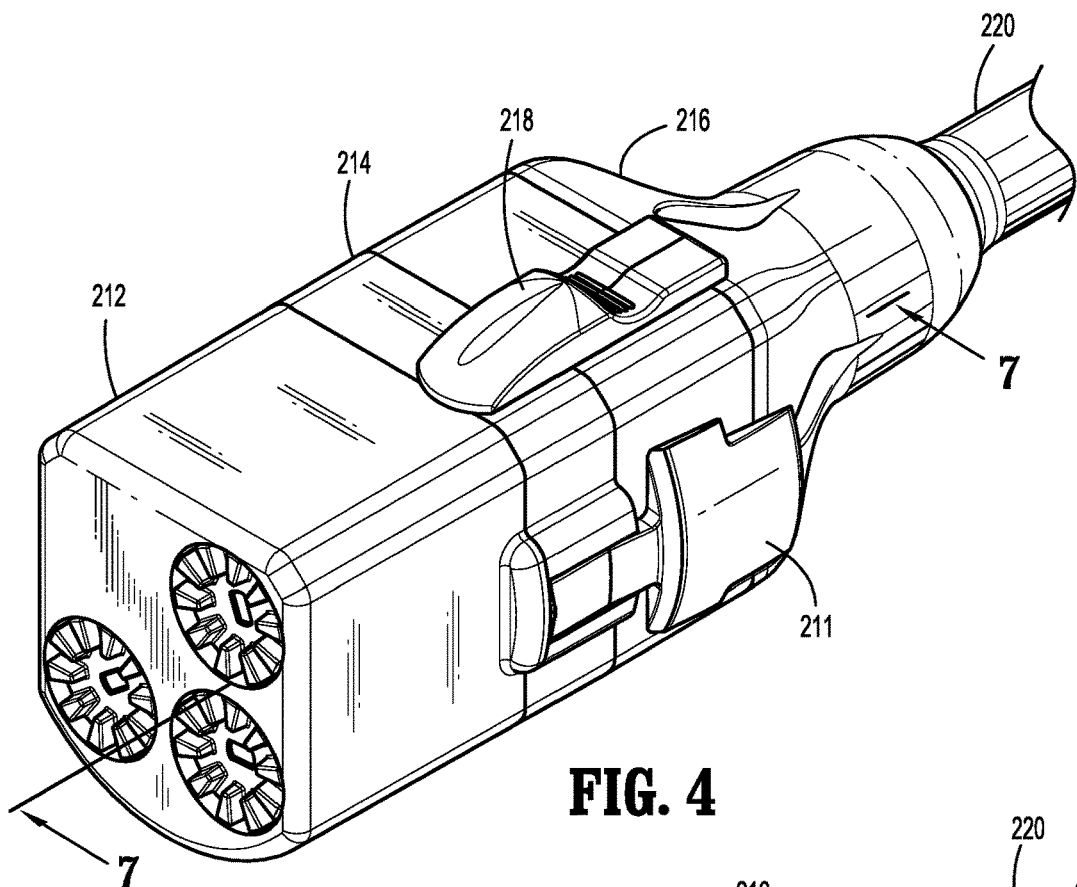
FIG. 4 is an enlarged perspective view of a housing assembly of the instrument drive connector of FIG. 3.
Figure 5:
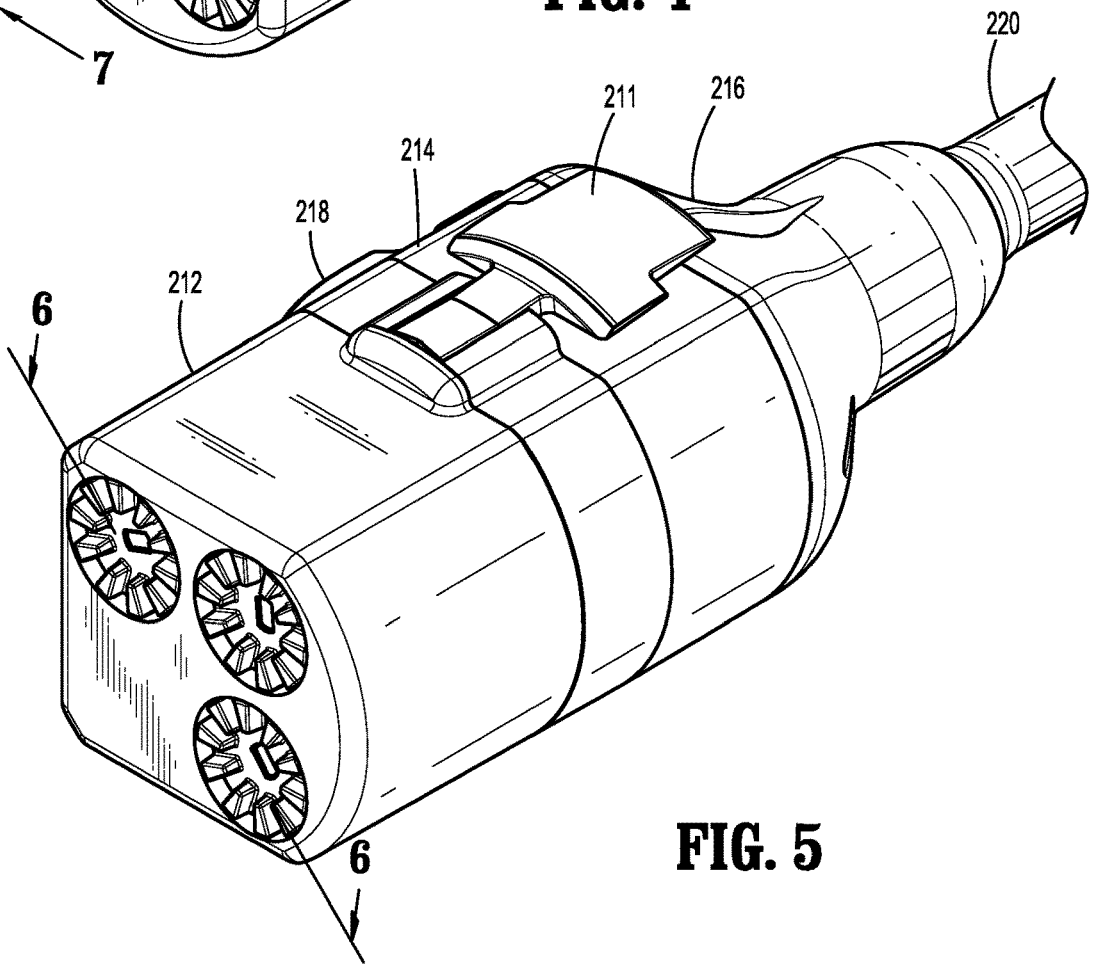
FIG. 5 is another enlarged perspective view of the housing assembly of the instrument drive connector of FIGS. 3 and 4.

Referring now to FIGS. 3-5, instrument drive connector 200 of surgical instrument 100 includes a housing assembly 210 and an elongated shaft 220 extending distally from the housing assembly 210 and terminating at a distal cap 222. Housing assembly 210 includes, from proximal to distal, a top or proximal housing 212, a bottom or distal housing 214, and a tip housing 216. Distal housing 214 including an aperture 214a (see e.g., FIG. 7) defined in a side surface thereof through which is disposed a finger switch 218. Proximal housing 212 and distal housing 214 are releasably coupled to each other, which may facilitate assembly of instrument drive connector 200, and which may facilitate access, repair, and/or replacement of parts housed at least partially therein. Housing assembly 210 may include cantilevered arms, levers, or paddles 211 configured for use in disconnecting instrument drive connector 200 from distal end 64 of housing 60 of instrument drive unit 50 (FIG. 2).

Figure 6:
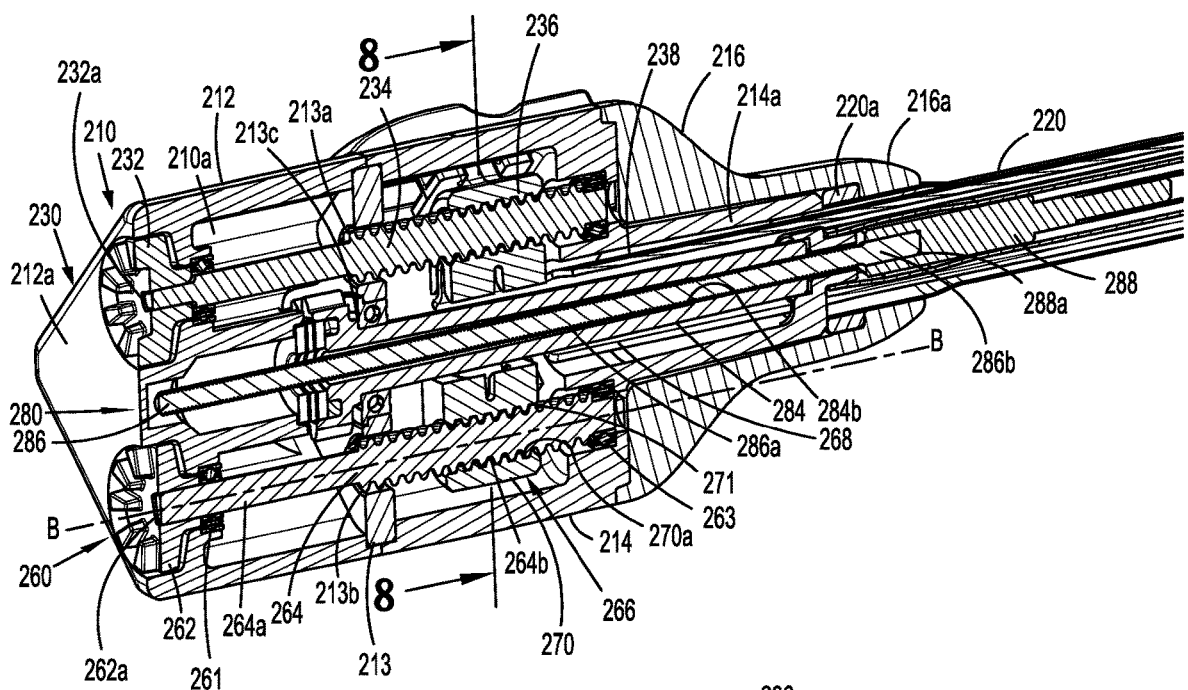
FIG. 6 is a cross-sectional view of the instrument drive connector of FIGS. 3-5, taken along line 6-6 of FIG. 5.

With reference now to FIG. 6, housing assembly 210 supports a first drive assembly 230, a second drive assembly 260, and a third drive assembly 280 for effecting a function of end effector 410 of surgical instrument 100 (FIG. 2). Housing assembly 210 defines a cavity 210a therein in which at least a portion of the first, second, and third drive assemblies 230, 260, and 280 are disposed. A plate 213 is disposed within cavity 210a between or at the junction of proximal and distal housings 212 and 214. Plate 213 defines a plurality of openings 213a-213c therethrough in which components of first, second, and third drive assemblies 230, 260, and 280 are disposed.

A proximal end portion 220a of elongated shaft 220 is disposed within a distal end portion 216a of tip housing 216 and a distal end 214b of distal housing 214 is pressed distally onto proximal end portion 220a of elongated shaft 220 to retain elongated shaft 220 securely between distal housing 214 and tip housing 216, thereby keeping the elongated shaft 220 straight and preventing shaft rotation.

Referring now to FIGS. 6-10, first drive assembly 230, also referred to herein as a locking assembly, includes a first input drive coupler 232, a first drive screw 234, a first drive nut 236, and a first drive member or locking link or shaft 238. First input drive coupler 232 is disposed at a proximal end 212a of proximal housing 212 of housing assembly 210 and is configured to engage an output drive coupler (not shown) of instrument drive unit 50 (FIG. 2). First input drive coupler 232 is configured to mechanically engage a proximal end of first drive screw 234. An aperture 232a defined through first input drive coupler 232 has a corresponding, non-circular cross-section with the proximal end of first drive screw 234 such that first input drive coupler 232 and first drive screw 234 are keyed to one another, which results in a rotationally fixed connection therebetween. Accordingly, rotation of first input drive coupler 232 results in a corresponding rotation of first drive screw 234.

First drive screw 234 includes a non-threaded proximal body portion 234a and a threaded distal body portion 234b, and defines a longitudinal axis "A" extending through a radial center thereof. Rotation of first input drive coupler 232 causes first drive screw 234 to rotate about longitudinal axis "A" in a corresponding direction and rate of rotation. A proximal bearing 231 is disposed about a proximal end of non-threaded proximal body portion 234a of first drive screw 234, adjacent a portion of proximal housing 212, and a distal bearing 233 is disposed about a distal end of threaded distal body portion 234b of first drive screw 234 adjacent a portion of distal housing 214. Proximal and distal bearings 231 and 233 permit or facilitate rotation of first drive screw 234 with respect to housing assembly 210 without causing longitudinal movement of first drive screw 234.

First drive nut 236 includes a body 240 having a threaded aperture 241 extending longitudinally through an inner surface 240a of body 240, which is configured to mechanically engage threaded distal body portion 234b of first drive screw 234. First drive nut 236 is configured to be positioned on first drive screw 234 in a manner such that rotation of first drive screw 234 causes longitudinal movement of first drive nut 236. In embodiments, first drive nut 236 and first drive screw 234 are threadedly engaged with each other. Moreover, rotation of first input drive coupler 232 in a first direction (e.g., clockwise) causes first drive nut 236 to move in a first longitudinal direction (e.g., proximally) with respect to first drive screw 234, and rotation of first input drive coupler 232 in a second direction (e.g., counterclockwise) causes first drive nut 236 to move in a second longitudinal direction (e.g., distally) with respect to first drive screw 234.

Figure 7:
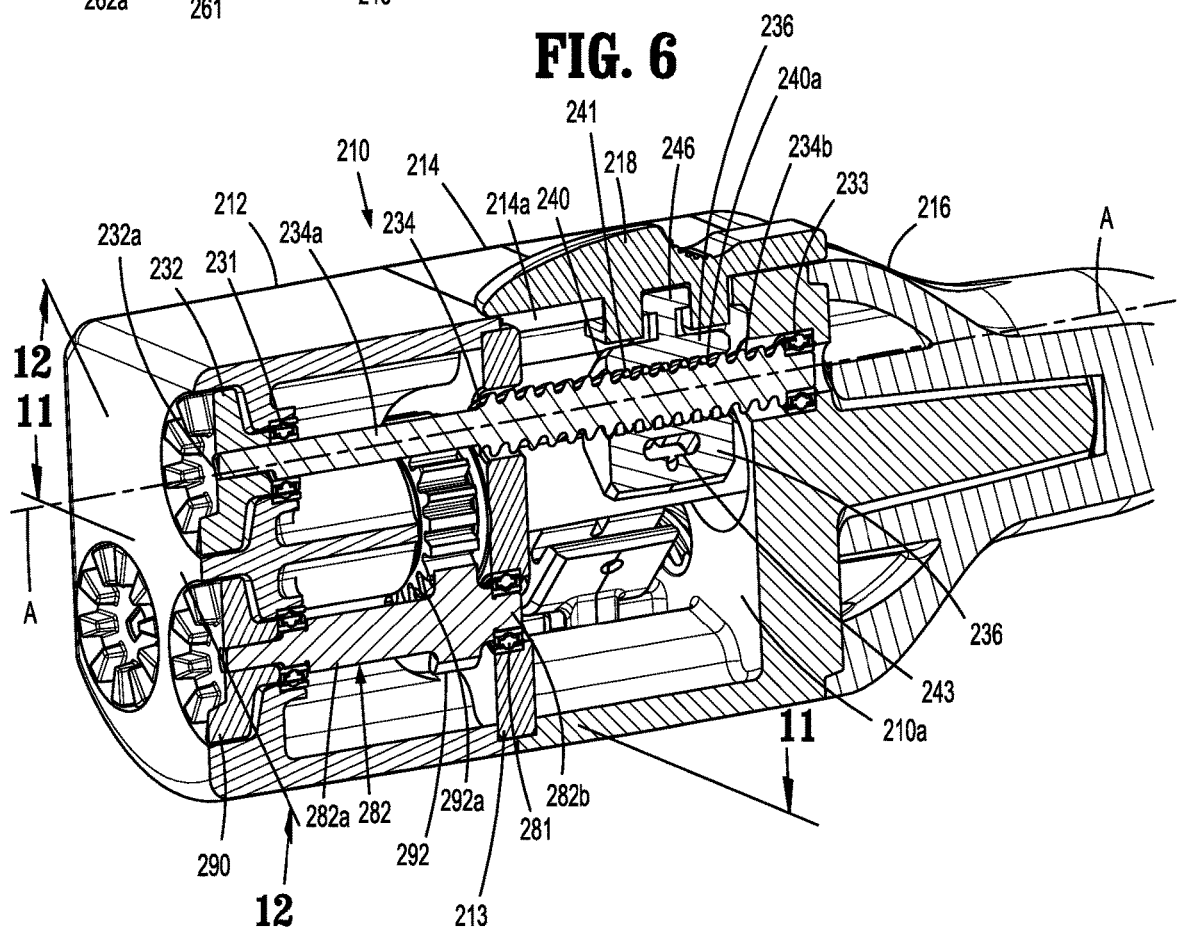
FIG. 7 is a cross-sectional view of the instrument drive connector of FIGS. 3-6, taken along line 7-7 of FIG. 4.
Figure 8:
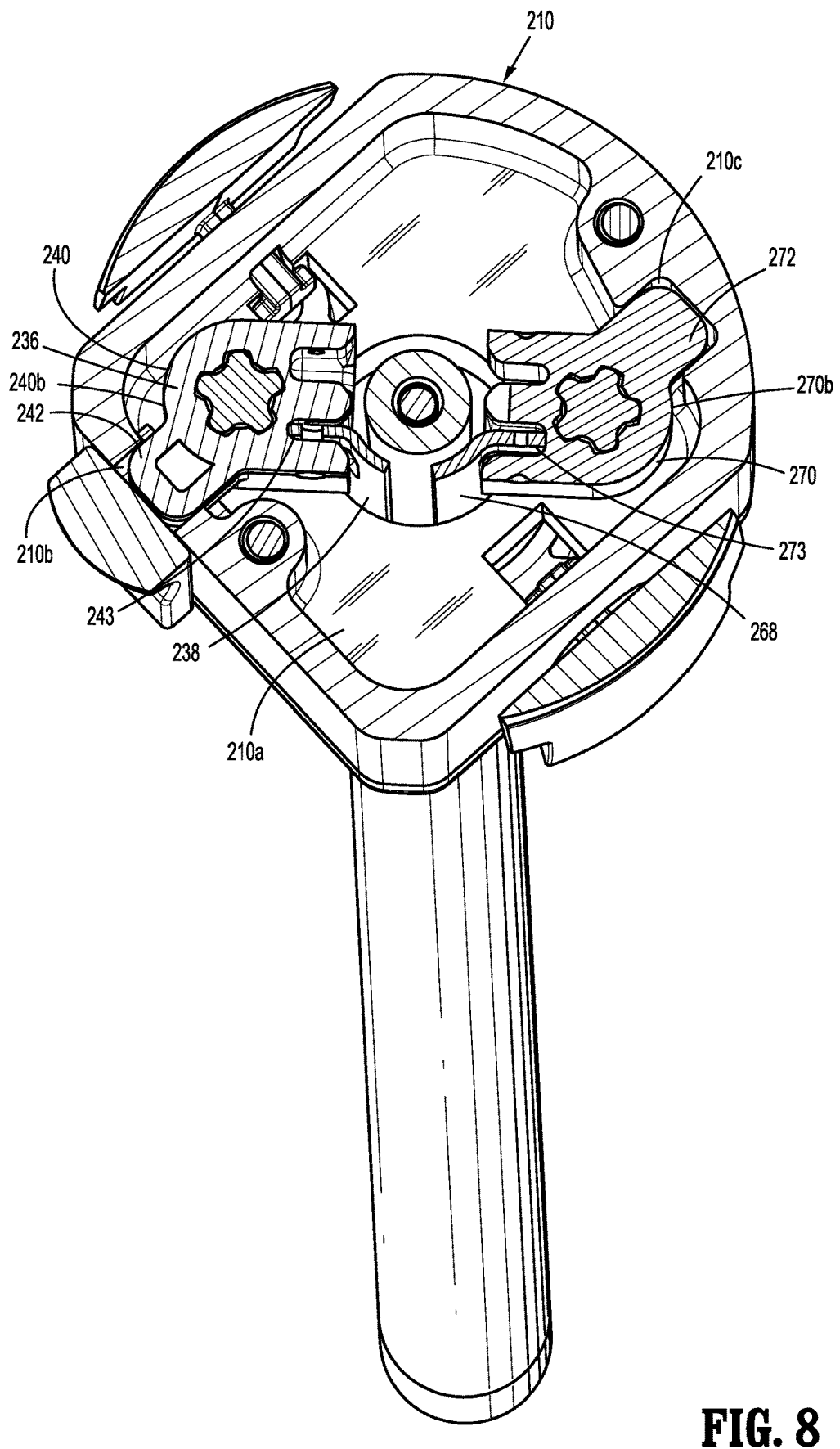
FIG. 8 is a cross-sectional view of the instrument drive connector of FIGS. 3-7, taken along line 8-8 of FIG. 6.

First drive nut 236 includes a tab or rail 242 extending longitudinally along the outer surface 240b of body 240, and which is configured to be slidably disposed in a longitudinally extending channel 210b formed in cavity 210a of housing assembly 210 (FIG. 8). Rail 242 of first drive nut 236 cooperates with channel 210b of housing assembly 210 to inhibit or prevent first drive nut 236 from rotating about longitudinal axis "A" as first drive screw 234 is rotated. First drive nut 236 includes a slit 243 defined in outer surface 240b of the body 240 that is configured for receipt and securement of a proximal end portion of locking link 238. A projection or rod 244 (FIGS. 9A and 9B) extends transversely through slit 243 and locking link 238 to retain locking link 238 within slit 243 of first drive nut 236. First drive nut 236 further includes a tab 246 extending laterally from body 240 of first drive nut 236 (FIG. 7). Tab 246 extends through aperture 214a formed in housing assembly 210 and into finger switch 218 for manual movement of first drive nut 236 by a clinician (if needed), as described in further detail below.

Figure 10:
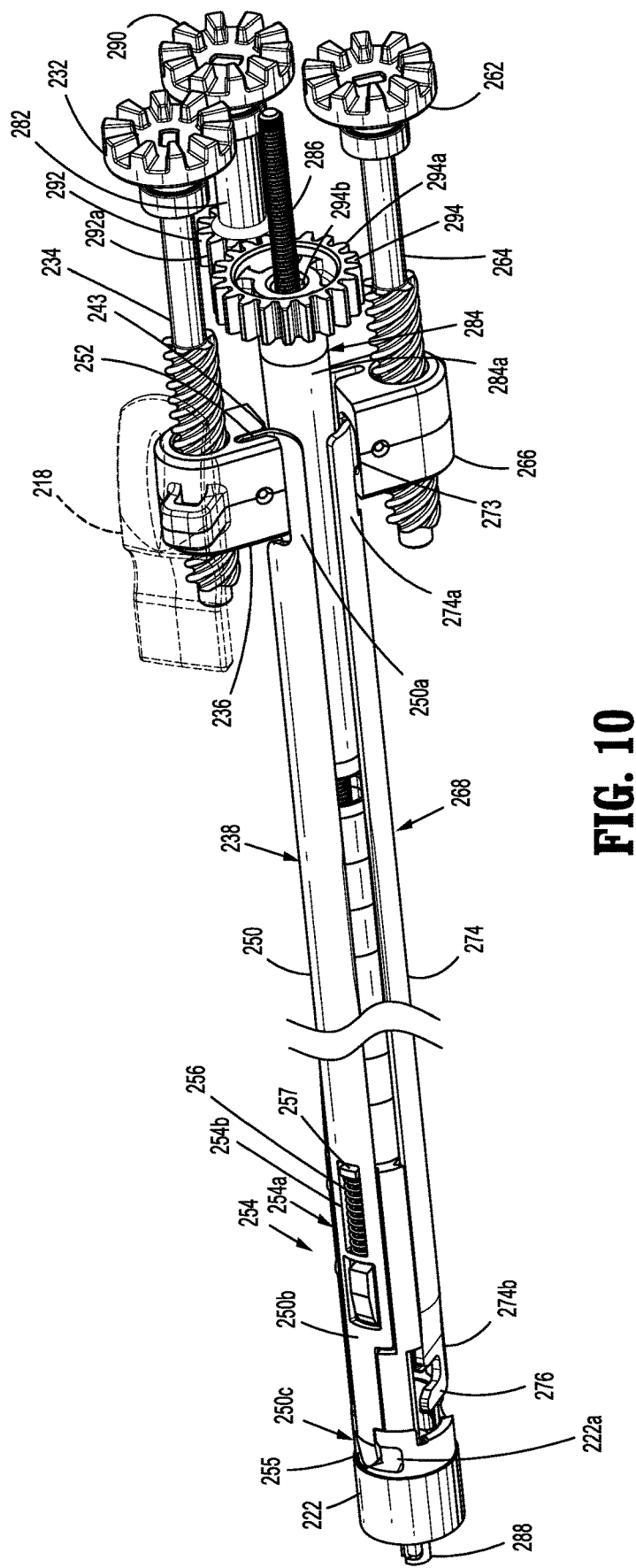
FIG. 10 is a perspective view, with parts removed, of internal components of the instrument drive connector of FIGS. 3-9B.
Figure 11:
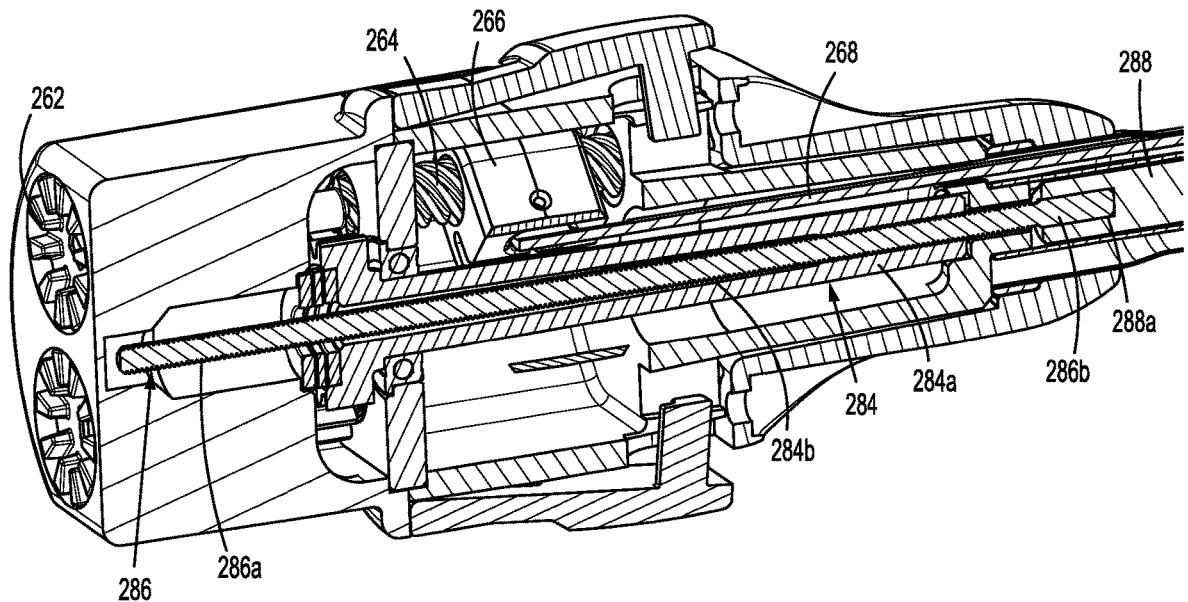
FIG. 11 is a cross-sectional view of the instrument drive connector of FIGS. 3-10, taken along line 11-11 of FIG. 7.
Figure 12:
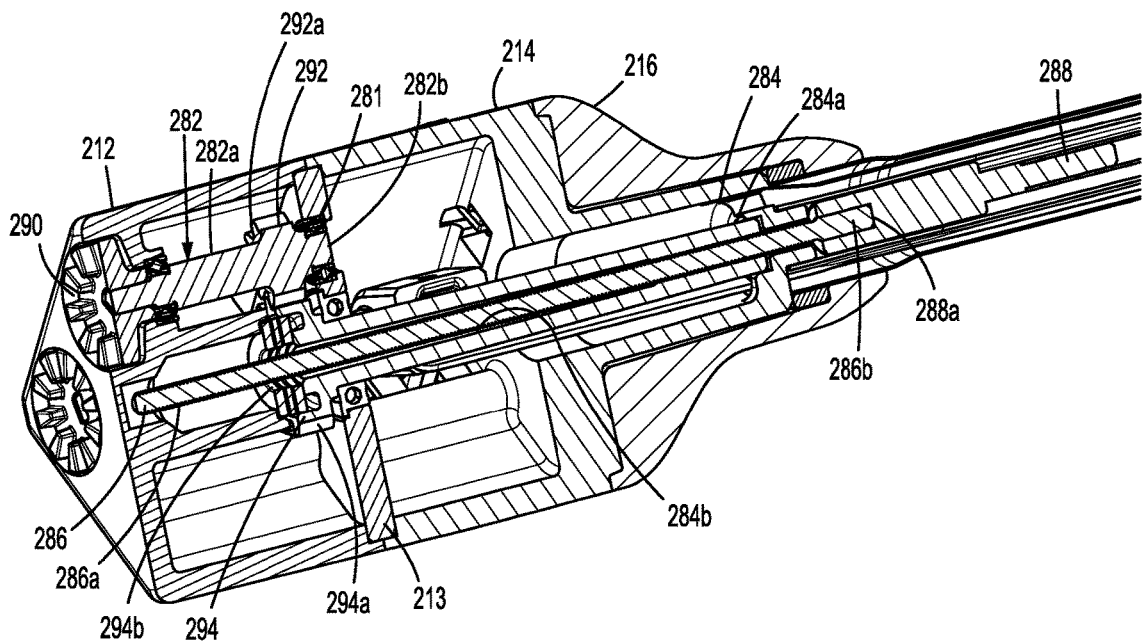
FIG. 12 is a cross-sectional view of the instrument drive connector of FIGS. 3-11, taken along line 12-12 of FIG. 7.

As illustrated in FIGS. 6 and 10, locking link 238 includes an elongated body 250 having a proximal end portion 250a and a distal end portion 250b. Proximal end portion 250a is securely engaged within slit 243 of first drive nut 236, as described above, such that longitudinal movement of first drive nut 236 causes a corresponding longitudinal movement of locking link 238. Locking link 238 extends distally through housing assembly 210 and elongated shaft 220, such that distal end portion 250b of elongated body 250 is disposed within elongated shaft 220 and movable between a locking position (FIG. 9A) and a non-locking position (FIG. 9B).

Proximal end portion 250a of locking link 238 has a laterally extending wing 252 movably disposed within slit 243 of first drive nut 236. Wing 252 of locking link 238 includes a longitudinal slot 252a formed therein. As described above, rod 244 of first drive nut 236 is disposed within longitudinal slot 252a of locking link 238 and rides within longitudinal slot 252a upon proximal or distal longitudinal movement of locking link 238 relative to first drive nut 236.

Longitudinal slot 252a of locking link 238 has a proximal end surface 252b and a distal end surface 252c. As such, when first drive nut 236 is in a distal locking position, as shown in FIG. 9A, rod 244 of first drive nut 236 is engaged with distal end surface 252c of longitudinal slot 252a of locking link 238 resisting or preventing locking link 238 from moving in a proximal direction from the distal locking position to a proximal non-locking position. When first drive nut 236 is in the proximal non-locking position, as shown in FIG. 9B, rod 244 of first drive nut 236 is disengaged from distal end surface 252c of longitudinal slot 252a of locking link 238 so as to no longer resist locking link 238 from moving in a proximal direction from the distal locking position to the proximal non-locking position.

Distal end portion 250b of elongated body 250 of locking link 238 includes a switch actuation assembly 254 proximal to an extension 255 disposed at a distalmost end 250c of elongated body 250 of locking link 238, as will be described in further detail below.

With reference now to FIGS. 6 and 8-11, second drive assembly 260, also referred to herein as an articulation assembly, includes a second input drive coupler 262, a second drive screw 264, a second drive nut 266, and a second drive member or articulation link or shaft 268. Second drive assembly 260 is substantially similar to the first drive assembly 230, and is only described herein to the extent necessary to identify the components thereof and to describe the differences in construction and operation thereof. Second input drive coupler 262 is configured to be detachably, non-rotatably coupled to the second drive screw 264, and includes an aperture 262a extending longitudinally therethrough, which is configured to mechanically engage and be keyed to a proximal portion of second drive screw 264 which results in a rotationally fixed connection therebetween.

Second drive screw 264 includes a non-threaded proximal body portion 264a and a threaded distal body portion 264b and defines a longitudinal axis "B" extending through a radial center thereof. A proximal bearing 261 is disposed about a proximal end of non-threaded proximal body portion 264a of second drive screw 264, and a distal bearing 263 is disposed about a distal end of threaded distal body portion 264b of second drive screw 264 to permit or facilitate rotation of second drive screw 264 about longitudinal axis "B" without permitting longitudinal movement of second drive screw 264.

Second drive nut 266 includes a body 270 having a threaded aperture 271 extending longitudinally through an inner surface 270a of body 270, which is configured to mechanically engage threaded distal body portion 264b of second drive screw 264. Second drive nut 266 includes a tab or rail 272 extending longitudinally along the outer surface 270b of body 270, and which is configured to be slidably disposed in a longitudinally extending channel 210c formed in cavity 210a of housing assembly 210 (FIG. 8). Second drive nut 266 includes a slit 273 defined in outer surface 270b of the body 270 that is configured for fixed receipt and securement of a proximal end of articulation link 268. As such, upon rotation of second drive screw 264, second drive nut 266 moves either proximally or distally along second drive screw 264 to effect a corresponding longitudinal movement of articulation link 268.

Articulation link 268 includes an elongated body 274 having a proximal end portion 274a and a distal end portion 274b. Proximal end portion 274 is securely engaged within slit 273 of second drive nut 266, as described above. Articulation link 268 extends distally through housing assembly 210 and elongated shaft 220, such that the distal end portion 274b of the elongated body 274 is disposed within shaft 220. Distal end portion 274b includes an extension 276, such as a j-hook, that is releasably couplable to end effector 410 (FIG. 2). Accordingly, rotation of second drive input coupler 262 causes a corresponding rotation of second drive screw 264, which in turn, effects a corresponding longitudinal movement of second drive nut 266 and articulation link 268, which in turn, effects articulation of an end effector to actuate, for example, a knife blade or a pair of jaws.

As shown in FIGS. 6, 7, and 10-12, third drive assembly 280, also referred to herein as a firing assembly, includes a proximal shaft 282, a distal shaft 284, a drive rod 286, and a drive shaft 288. Proximal shaft 282 includes a non-threaded shaft body 282a including a third input drive coupler 290 disposed at a proximal end thereof and a distal gear 292 having a plurality of gear teeth 292a disposed at a distal end of non-threaded shaft body 282a. Third input drive coupler 290 and distal gear 292 are non-rotatably secured to shaft body 282a such that rotation of third input drive coupler 290 results in a corresponding rotation of shaft body 282a and distal gear 292. A distalmost end 282b of proximal shaft 282 is secured within a bearing 281 disposed within plate 213 of housing assembly 210 such that proximal shaft 282 will rotate without longitudinal movement.

Distal shaft 284 includes a proximal gear 294 non-rotatably secured to an elongated non-threaded shaft body 284a. Teeth 292a of distal gear 292 of proximal shaft 292 is meshingly engaged with teeth 294a of proximal gear 294 of distal shaft 284 such that rotation of distal gear 292 results in a corresponding rotation of proximal gear 294, which in turn, results in rotation of shaft body 284a of distal shaft 284. A distal end of shaft body 284a of distal shaft 284 abuts an inner surface of distal housing 214 such that rotation of distal shaft 284 does not result in axial translation of distal shaft 284.

Proximal gear 294a defines a central aperture 294b that is aligned with a threaded channel 284b defined in shaft body 284a of distal shaft 284, and extends the entire longitudinal length of distal shaft 284. Drive rod 286 includes a threaded elongated body 286a and is configured to mechanically engage the threaded channel 284b of shaft body 284a of distal shaft 284 in such a manner that rotation of shaft body 284a causes longitudinal movement of drive rod 286. That is, threaded channel 284b of shaft body 284a of distal shaft 284 and threaded elongated body 286a of drive rod 286 are threadedly engaged with each other. Moreover, rotation of distal shaft 284 in a first direction (e.g., clockwise) causes drive rod 286 to move in a first longitudinal direction (e.g., proximally) with respect to distal shaft 284, and rotation of drive shaft 284 in a second direction (e.g., counter-clockwise) causes drive rod 286 to move in a second longitudinal direction (e.g., distally) with respect to distal shaft 284. Drive rod 286 includes a non-threaded distal end 286b that is keyed to a recess 288a defined in a proximal end of drive shaft 288 such that longitudinal movement of drive rod 286 causes a corresponding longitudinal movement of drive shaft 288 to effect a function of end effector 410, such as firing of staple(s) (FIG. 2).

Figure 13:
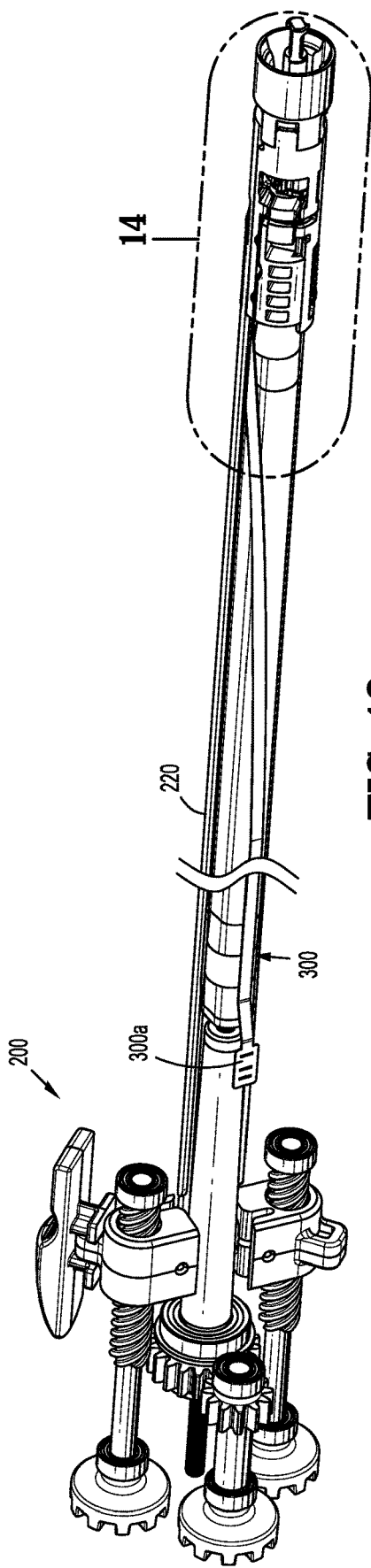
FIG. 13 is a perspective view, with parts removed, of internal components of the instrument drive connector of FIGS. 3-12.
Figure 14:
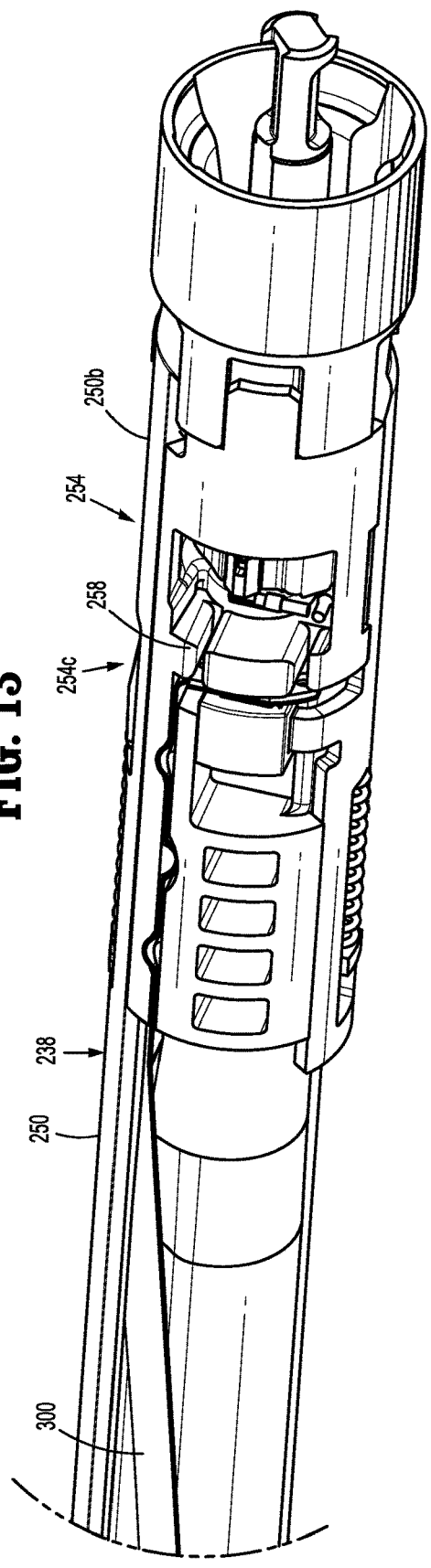
FIG. 14 is an enlarged view of the area of detail indicated in FIG. 13.

Referring now to FIGS. 13-15, a flexible circuit or flex circuit 300 is disposed within elongated shaft 220 of instrument drive connector 200 and is configured to electrically connect electrical components of instrument drive connector 200 and/or end effector 410 (FIG. 2) to a processor of instrument drive unit 50 and/or medical workstation 1 (FIG. 1). The flex circuit 300 is easily to assemble within instrument drive connector 200 and eliminates the need for discreet, separate wires, ultimately enhancing patient safety and reducing manufacturing costs. Flex circuit 300 extends longitudinally through the elongated shaft 220 and has a proximal end 300a and a distal end 300b. Proximal end 300a of flex circuit 300 is configured for electrical communication with contacts or the like (not shown) provided in proximal housing 212 of instrument drive connector 200. Distal end 300b of flex circuit 300 terminates at a switch 310 which is oriented in a distal facing direction and configured to be activated upon proper connection of surgical loading unit 400 (FIG. 2) to instrument drive connector 200. Switch 310 communicates with the processor of medical work station 1 (FIG. 1) that surgical loading unit 400 is engaged to, or disengaged with, the elongated shaft 220 of instrument drive connector 200.

Switch 310 is in operative communication with the switch actuation assembly 254 disposed at the distal end portion 250b of elongated body 250 of locking link 238. As shown in FIGS. 10 and 13-15, switch actuation assembly 254 includes a proximal end portion 254a that defines an elongated opening 254b have a coil spring 256 disposed therein. Coil spring 256 is secured within the elongated opening 254b between a distal end of an inner surface 254c of the elongated opening 254b and a projection 257 which projects through the elongated opening 254b. Switch actuation assembly 254 further includes a distal end portion 254c including a switch actuating arm 258 that is longitudinally movable between a proximal position and a distal position upon movement of elongated body 250 of locking link 238. Coil spring 256 resiliently biases the switch actuating arm 258 distally so that the arm 258 is distal of switch 310 and maintained in the proximal non-locking position of FIG. 9B, unless held in another different position, as described in further detail below.

With reference now to FIG. 16, in conjunction with FIG. 15, an annular member 320 is also disposed within the elongated shaft 220. Annular member 320 extends from a proximal end 320a to a distal end 320b and defines a cylindrical passageway therethrough. Proximal end 320a includes a first ring 322 and distal end 320b includes a second ring 324, spaced from the first ring 322 along a longitudinal bar 325 extending along a length of the annular member 320. First ring 322 includes a pair of electrical contacts 326a and 326b electrically coupled to switch 310 via wires 328. Electrical contacts 326a and 326b are configured to engage corresponding electrical contacts of a surgical loading unit 400, such that switch 310 and annular member 320 are capable of transferring data pertaining to surgical loading unit 400 therebetween. For example, electrical contacts 326a and 326b may be configured to couple to a memory (not shown) disposed within surgical loading unit 400, which is configured to store data pertaining to surgical loading unit 400 and to provide said data to flex circuit 300 in response to surgical loading unit 400 being coupled to instrument drive connector 200. Second ring 324 is configured and dimensioned to receive a proximal end of surgical loading unit 400 and to interface with surface features of surgical loading unit 400 so that annular member 320 is rotatable by and with surgical loading unit 400.

Instrument drive connector 200 has a load state, an unload state, and a locked state. The load state allows a surgical loading unit 400 to be freely inserted into instrument drive connector 200. The unload state allows a surgical loading unit 400 to be freely removed from instrument drive connector 200. The unload state requires a clinician to deliberately twist and pull surgical loading unit 400 from instrument drive connector 200 ensuring that at no time surgical loading unit 400 can fall off instrument drive connector 200. In the locked state, a surgical loading unit 400 cannot be either inserted or removed from instrument drive connector 200.

With reference to FIGS. 1, 2, 9A, 9B, and 10, to load surgical loading unit 400 onto instrument drive connector 200, instrument drive connector 200 is switched (either manually or automatically) to a loading state, in which locking link 238 of instrument drive connector 200 is free to move from the distal locking position (FIG. 9A), to the proximal non-locking position (FIG. 9B). In particular, an output drive coupler (not shown) of instrument drive unit 50 operatively engaged with first input drive coupler 232 is manually or automatically activated to drive rotation of first drive screw 234 of instrument drive connector 200 via first input drive coupler 232. Rotation of first drive screw 234 longitudinally moves first drive nut 236 proximally along first drive screw 234 from the distal position, shown in FIG. 9A, to the proximal position, shown in FIG. 9B. As first drive nut 236 moves proximally along first drive screw 234, rod 244 of first drive nut 236 moves longitudinally through longitudinal slot 252a of locking link 238 to disengage from distal end surface 252c of longitudinal slot 252a of locking link 238.

With first drive nut 236 in the proximal position and rod 244 of first drive nut 236 out of engagement with distal end surface 252c of longitudinal slot 252a of locking link 238, rod 244 of first drive nut 236 no longer resists proximal longitudinal movement of locking link 238. As such, an application of a force on extension 255 of locking link 238 by a lug (not shown) of surgical loading unit 400, in a proximal direction, effects proximal longitudinal movement of locking link 238 to move locking link 238 from the distal locking position to the proximal non-locking position.

Surgical loading unit 400 is then rotated to position the lug (not shown) of surgical loading unit 400 within inner groove 222a of distal cap 222 of elongated shaft 220. Upon rotation, the distal resilient bias of locking link 238 causes locking link 238 to move distally relative to elongated shaft 220 to the distal locking position, in which extension 255 of locking link 238 prevents the lug and thus surgical loading unit 400 from rotating out of the enclosed inner groove 222a. As such, surgical loading unit 400 is lockingly coupled to instrument drive connector 200 and ready for use.

Upon loading surgical loading unit 400, medical work station 1 may perform integrity checks to assure that surgical loading unit 400 was correctly loaded onto instrument drive connector 200. These checks could include, for example, retracting a knife bar and/or ensuring it cannot move in a direction it was not designed to move (which would indicate a misload), checking the range of articulation or load links, etc. The integrity checks could be performed before or during attempts to lower surgical instrument 100 into a patient "P". If medical work station 1 detects a misload, it could lock out slider 11 such that the surgical assembly 10 cannot be inserted into the patient "P". Instrument drive connector 200 may also enter the unload state and the medical work station 1 would prompt the clinician to reload surgical loading unit 400.

Once surgical loading unit 400 is coupled to instrument drive connector 200, it may be beneficial to prevent inadvertent removal of surgical loading unit 400 from instrument drive connector 200. To prevent this, instrument drive connector 200 may be switched from the load state to the locked state. In some embodiments, it is envisioned that a computer, for example control device 4 may be programmed to automatically activate instrument drive unit 50 to switch instrument drive connector 200 to the locked state upon control device 4 detecting that surgical loading unit 400 is successfully coupled to instrument drive connector 200. For example, upon successful load, medical work station 1 will automatically switch to a locked state when end effector 410 of the surgical loading unit 400 enters an access port (not shown) disposed inside a patient's body or is a predetermined distance from the patient "P". In some embodiments, a clinician, upon successfully coupling surgical loading unit 400 to instrument drive connector 200, may activate instrument drive unit 50 to switch instrument drive connector 200 to the locked state. By providing medical work station 1 with the ability to selectively lock surgical loading unit 400 with instrument drive connector 200, any possibility of releasing or dropping surgical loading unit 400 is removed.

Upon proper connection of surgical loading unit 400 with instrument drive connector 200, flex circuit 300 automatically transmits the operating parameters stored in a memory (not shown) to the processor. If surgical loading unit 400 is not properly connected to instrument drive connector 200, or the wrong surgical loading unit 400 is connected to instrument drive connector 200, switch 310 of flex circuit 300 will not be activated such that surgical instrument 100 will not be operable to actuate functions of surgical loading unit 400.

To switch instrument drive connector 200 to the locked state, thereby locking surgical loading unit 400 thereto, first drive nut 236 of instrument drive connector 200 is moved to the distal locking position (FIG. 9A). In the distal locking position, first drive nut 236 resists proximal longitudinal movement of locking link 238 from the distal locking position to the proximal non-locking position, in which surgical loading unit 400 may be inadvertently removed from instrument drive connector 200. To move first drive nut 236 to the distal locking position, an output drive coupler (not shown) of instrument drive unit 50 is activated (either manually or automatically) to drive rotation of first drive screw 234 of instrument drive connector 200 via first input drive coupler 232. Rotation of first drive screw 234 longitudinally moves first drive nut 236 distally along first drive screw 234 from the proximal position, shown in FIG. 9B, to the distal position, shown in FIG. 9A. As first drive nut 236 moves distally along first drive screw 234, rod 244 of first drive nut 236 moves longitudinally through longitudinal slot 252a of locking link 238 and into engagement with distal end surface 252c of longitudinal slot 252a of locking link 150.

With first drive nut 236 in the distal position, and rod 244 of first drive nut 236 engaged with distal end surface 252c of longitudinal slot 252a of locking link 238, rod 244 of first drive nut 236 resists proximal longitudinal movement of locking link 238. As such, inadvertent application of a force on locking link 238, in a proximal direction will not move locking link 238 out of the distal locking position and into the proximal non-locking position.

To remove surgical loading unit 400 from instrument drive connector 200, instrument drive connector 200 is switched (either manually or automatically) to an unload state, in which locking link 238 is moved back to the proximal non-locking position. In embodiments, the unload state will occur when instrument drive connector 200 is removed from a patient "P" with a used surgical loading unit 400 attached. Once the surgical loading unit 400 is safely above an access port (not shown) or end effector 410 is a predetermined distance from the patient "P", medical work station 1 will automatically switch the state of instrument drive connector 200. In the unload state, a clinician can remove surgical loading unit 400. Entering the unload state may depend on whether surgical loading unit 400 was fired. In some embodiments, medical work station 1 may be configured to prevent instrument drive connector 200 from entering the unload state if surgical loading unit 400 was not fired, which would require a clinician to manually unload surgical loading unit 400 through a conventional interface, such as interfacing with a component (e.g., a surgeon console, nurse tower, or dedicated button) of medical work station 1. In some embodiments, a clinician may choose to manually switch between the load and unload states through a conventional interface if surgical loading unit 400 did not fire or the wrong surgical loading unit 400 was loaded.

A situation may arise (e.g., an emergency or system default) in which the instrument drive connector 200 is not able to switch from the locked state to the unload state such that surgical loading unit 400 cannot be removed from instrument drive connector 200 via instrument drive unit 50. Accordingly, in embodiments in which the locked state is enforced by the instrument drive unit 50, removing instrument drive unit 50 from the medical work station 1 will allow surgical loading unit 400 to be removed from instrument drive connector 200. In this situation, to remove surgical loading unit 400 from instrument drive connector 200, instrument drive unit 50 is first detached from housing assembly 210 of instrument drive connector 200. A clinician may then manually move finger switch 218 of first drive nut 236 in a proximal direction by applying a threshold amount of force on finger switch 218. It can be appreciated that because first drive nut 236 is threadedly engaged to first drive screw 234, it cannot move therealong without being rotated. However, first drive screw 234 may be axially movable in a proximal direction relative to housing assembly 210 when instrument drive unit 55 is not engaged to housing 210. Accordingly, as a clinician applies a proximally-oriented force on first drive nut 236, first drive screw 234 moves in a proximal direction with first drive nut 236 to allow first drive nut 236 to be manually moved to the proximal non-locking position.

As first drive nut 236 is manually moved in a proximal direction, rod 244 of first drive nut 236 engages proximal end surface 252b of longitudinal slot 252a of locking link 238, moving locking link 238 in the proximal direction into the proximal non-locking position. With locking link 238 in the proximal non-locking position, surgical loading unit 400 may be removed by rotating surgical loading unit 400 and then moving surgical loading unit 400 in a distal direction out of distal cap 222 of instrument drive connector 200.

In some embodiments, an array of lights (not shown) may be provided on any or all of the components of robotic arm 2, instrument drive unit 50, instrument drive connector 200 of surgical assembly 10, and/or a surgical robotic cart (not shown) configured for supporting at least one robotic arm 2. These lights may indicate the status of the surgical instrument, for example: the robotic arm is in patient with no errors (ready to retract for exchange of the surgical loading unit); the robotic arm is in the patient with an error (cannot retract the surgical loading unit); or the robotic arm is out of the patient and in an unload state, a locked state, a load state waiting for the surgical loading unit, a load state having a successfully loaded surgical loading unit, or an unloaded state having a misloaded surgical loading unit.

A number of embodiments have been described. Nevertheless, it will be understood that various modifications may be made to the embodiments disclosed herein. Therefore, the above description should not be construed as limiting, but merely as exemplifications of various embodiments. Those skilled in the art will envision other modifications within the scope and spirit of the disclosure. Accordingly, other embodiments are within the scope of the following claims.

What is claimed is:
1. A surgical assembly, comprising:
an instrument drive unit;
a surgical loading unit including an end effector; and an instrument drive connector interconnecting the instrument drive unit and the surgical loading unit, the instrument drive connector including:
- a locking link longitudinally movable between a proximal non-locking position and a distal locking position,
- a drive screw operably coupled to the instrument drive unit, and
- a drive nut coupled to the drive screw and longitudinally movable relative thereto in response to rotation of the drive screw, wherein the locking link is coupled to the drive nut and is longitudinally movable by the drive nut,
- wherein the instrument drive connector operable in:
  - a load state in which the locking link is movable relative to the drive nut between the non-locking and locking positions such that the surgical loading unit is couplable to the instrument drive connector;
  - an unload state in which the locking link is in the non-locking position such that the surgical loading unit is detachable from the instrument drive connector; and
  - a locked state in which the locking link is in the locking position such that the surgical loading unit is secured to the instrument drive connector, and wherein the drive nut prevents the locking link from moving to the non-locking position.

2. The surgical assembly according to claim 1, wherein the instrument drive connector further includes a finger switch coupled to the locking link.

3. The surgical assembly according to claim 2, wherein in the unload state, the locking link is movable by the instrument drive unit or by the finger switch.

4. The surgical assembly according to claim 1, wherein the instrument drive connector further includes a switch engageable by the surgical loading unit.

5. The surgical assembly according to claim 4, wherein the switch is electrically coupled to the instrument drive unit and is configured to output an activation signal indicating whether the surgical loading unit is coupled to the instrument drive connector.

6. The surgical assembly according to claim 5, wherein the instrument drive unit is configured to operate the instrument drive connector based on the activation signal.

7. The surgical assembly according to claim 6, wherein the surgical loading unit includes at least one lug, and the instrument drive connector includes a distal connection cap having at least one groove configured to receive the at least one lug.

8. The surgical assembly according to claim 7, wherein the surgical loading unit is coupled to the instrument drive connector by inserting a proximal portion of the surgical loading unit into the distal connection cap and then rotating the surgical loading unit.

9. The surgical assembly according to claim 8, wherein the at least one lug is configured to move the locking link distally upon coupling the surgical loading unit to the instrument drive connector thereby activating the switch.

10. A surgical robotic arm comprising:
an instrument drive unit including a motor;
a surgical loading unit including an end effector; and
an instrument drive connector interconnecting the instrument drive unit and the surgical loading unit, the instrument drive connector including:
- a locking link longitudinally movable by the motor between a proximal non-locking position and a distal locking position,
- a drive screw operably coupled to the motor, and
- a drive nut coupled to the drive screw and longitudinally movable relative thereto in response to rotation of the drive screw by the motor, wherein the locking link is coupled to the drive nut and is longitudinally movable by the drive nut,
- wherein the instrument drive connector operable in:
  - a load state in which the locking link is movable relative to the drive nut between the non-locking and locking positions such that the surgical loading unit is couplable to the instrument drive connector;
  - an unload state in which the locking link is in the non-locking position such that the surgical loading unit is detachable from the instrument drive connector; and
  - a locked state in which the locking link is in the locking position such that the surgical loading unit is secured to the instrument drive connector, and wherein the drive nut prevents the locking link from moving to the non-locking position.

11. The surgical robotic arm according to claim 10, wherein the instrument drive connector further includes a finger switch coupled to the locking link.

12. The surgical robotic arm according to claim 11, wherein in the unload state, the locking link is movable by the instrument drive unit or by the finger switch.

13. The surgical robotic arm according to claim 10, wherein the instrument drive connector further includes a switch engageable by the surgical loading unit.

14. The surgical robotic arm according to claim 13, wherein the switch is electrically coupled to the instrument drive unit and is configured to output an activation signal indicating whether the surgical loading unit is coupled to the instrument drive connector.

15. The surgical robotic arm according to claim 14, wherein the instrument drive unit is configured to operate the instrument drive connector based on the activation signal.

16. The surgical robotic arm according to claim 15, wherein the surgical loading unit includes at least one lug, and the instrument drive connector includes a distal connection cap having at least one groove configured to receive the at least one lug.

17. The surgical robotic arm according to claim 16, wherein the surgical loading unit is coupled to the instrument drive connector by inserting a proximal portion of the surgical loading unit into the distal connection cap and then rotating the surgical loading unit.

18. The surgical robotic arm according to claim 17, wherein the at least one lug is configured to move the locking link distally upon coupling the surgical loading unit to the instrument drive connector thereby activating the switch.

19. A surgical robotic arm comprising:
an instrument drive unit including a motor;
a surgical loading unit including an end effector; and
an instrument drive connector interconnecting the instrument drive unit and the surgical loading unit, the instrument drive connector including:
- a locking link longitudinally movable by the motor between a proximal non-locking position and a distal locking position,
- a drive screw operably coupled to the instrument drive unit, and
- a drive nut coupled to the drive screw and longitudinally movable relative thereto in response to rotation of the drive screw, wherein the locking link is coupled to the drive nut and is longitudinally movable by the drive nut, wherein the instrument drive connector operable by the instrument drive unit to be in:

a load state in which the locking link is movable relative to the drive nut between the non-locking and locking positions such that the surgical loading unit is couplable to the instrument drive connector; and an unload state in which the locking link is in the non-locking position such that the surgical loading unit is detachable from the instrument drive connector, and wherein the drive nut is configured to prevent the locking link from moving to the non-locking position.

* * * * *